(12) United States Patent  (10) Patent No.: US 7,854,227 B2
Djupesland  (45) Date of Patent: Dec. 21, 2010

(54) NASAL DEVICES

(75) Inventor: Per Gisle Djupesland, Oslo (NO)

(73) Assignee: OptiNose AS, Oslo (NO)

( * ) Notice: Subject to any disclaimer, the term of this patent is extended or adjusted under 35 U.S.C. 154(b) by 1416 days.

(21) Appl. No.: 10/512,514

(22) PCT Filed: Apr. 25, 2003

(86) PCT No.: PCT/IB03/02305

§ 371 (c)(1),
(2), (4) Date: Sep. 6, 2005

(87) PCT Pub. No.: WO03/090812

PCT Pub. Date: Nov. 6, 2003

(65) Prior Publication Data

US 2006/0096589 A1  May 11, 2006

(30) Foreign Application Priority Data

Apr. 25, 2002 (GB) ................. 0209494.4

(51) Int. Cl.
A61M 16/00 (2006.01)
A61M 15/00 (2006.01)
A61M 15/08 (2006.01)
B05D 7/14 (2006.01)
B65D 83/06 (2006.01)

(52) U.S. Cl. ............. 128/203.18; 128/203.15
(58) Field of Classification Search ............ 128/200.14, 128/200.17–200.23, 203.12–203.15, 203.18, 128/203.22, 203.23, 203.24, 207.18
See application file for complete search history.

(56) References Cited

U.S. PATENT DOCUMENTS 2,470,297 A   5/1949  Fields
3,324,852 A * 6/1967  Ryohei ............... 128/200.17
3,971,377 A   7/1976  Damani (Continued)

FOREIGN PATENT DOCUMENTS

DE   4208880   9/1993

(Continued)

OTHER PUBLICATIONS

U.S. Appl. No. 11/567,286, filed Dec. 6, 2006, Djupesland.

(Continued)

*Primary Examiner*—Justine R Yu
*Assistant Examiner*—Kristen C Matter
(74) *Attorney, Agent, or Firm*—Proskauer Rose LLP; Kristin Neuman, Esq.; Isaac A. Hubner, Esq.

(57) ABSTRACT

A nasal delivery device and method are provided for delivering substance to a nasal airway of a subject, in particular one of a liquid, as a suspension or solution, or a powder containing a medicament, especially systemic or topical pharmaceuticals, or a vaccine to the nasal airway of a subject. The delivery device is characterized by: a nosepiece for fitting to a nostril of a subject; a delivery unit including a substance supply unit and a nozzle unit including at least one nozzle fluidly connected to the substance supply unit for generating an aerosol spray for delivery to a nasal airway of the subject; and an aerosol interactor operable to interact with an aerosol spray as generated by the at least one nozzle.

52 Claims, 16 Drawing Sheets

U.S. PATENT DOCUMENTS

| | | | |
|---|---|---|---|
| 4,739,754 A | 4/1988 | Shaner | |
| 5,040,527 A | 8/1991 | Larson et al. | |
| 5,161,524 A | 11/1992 | Evans | |
| 5,178,138 A | 1/1993 | Walstrom et al. | |
| 5,301,666 A * | 4/1994 | Lerk et al. | 128/203.15 |
| 5,503,144 A | 4/1996 | Bacon | |
| 5,676,130 A | 10/1997 | Gupte et al. | |
| 6,347,629 B1 | 2/2002 | Braithwaite | |
| 6,681,768 B2 * | 1/2004 | Haaije de Boer et al. | 128/203.15 |
| 6,715,485 B1 | 4/2004 | Djupesland | |
| 7,347,201 B2 | 3/2008 | Djupesland | |
| 7,377,901 B2 | 5/2008 | Djupesland et al. | |
| 7,481,218 B2 | 1/2009 | Djupesland | |
| 2004/0112378 A1 | 6/2004 | Djupesland | |
| 2004/0112379 A1 | 6/2004 | Djupesland | |
| 2004/0149289 A1 | 8/2004 | Djupesland | |
| 2004/0182388 A1 | 9/2004 | Djupesland | |
| 2005/0028812 A1 | 2/2005 | Djupesland | |
| 2005/0072430 A1 | 4/2005 | Djupesland | |
| 2005/0235992 A1 | 10/2005 | Djupesland | |
| 2006/0169278 A1 | 8/2006 | Djupesland | |
| 2006/0219240 A1 | 10/2006 | Djupesland | |
| 2006/0219241 A1 | 10/2006 | Djupesland | |
| 2006/0225732 A1 | 10/2006 | Djupesland | |
| 2006/0231094 A1 | 10/2006 | Djupesland | |
| 2007/0039614 A1 | 2/2007 | Djupesland | |
| 2007/0125371 A1 | 6/2007 | Djupesland | |
| 2007/0186927 A1 | 8/2007 | Djupesland et al. | |
| 2008/0161771 A1 | 7/2008 | Djupesland | |
| 2008/0163874 A1 | 7/2008 | Djupesland | |
| 2008/0221471 A1 | 9/2008 | Djupesland | |
| 2008/0223363 A1 | 9/2008 | Djupesland | |
| 2008/0289629 A1 | 11/2008 | Djupesland | |
| 2009/0101146 A1 | 4/2009 | Djupesland | |

FOREIGN PATENT DOCUMENTS

| | | |
|---|---|---|
| EP | 0911048 | 4/1999 |
| EP | 1142601 | 10/2001 |
| GB | 1118341 | 7/1968 |
| GB | 2354451 | 3/2001 |
| WO | 97/41910 | 11/1997 |
| WO | 98/26827 | 6/1998 |
| WO | 00/09188 | 2/2000 |
| WO | 00/51672 | 9/2000 |
| WO | 02/04054 | 1/2002 |

OTHER PUBLICATIONS

U.S. Appl. No. 11/816,984, filed Aug. 23, 2007, Djupesland.
U.S. Appl. No. 12/161,466, filed Jul. 18, 2008, Djupesland.
U.S. Appl. No. 12/279,285, filed Aug. 13, 2008, Djupesland.
U.S. Appl. No. 12/279,291, filed Aug. 13, 2008, Djupesland.
U.S. Appl. No. 12/281,547, filed Sep. 3, 2008, Djupesland.
U.S. Appl. No. 12/281,894, filed Sep. 5, 2008, Djupesland.
U.S. Appl. No. 12/293,972, filed Sep. 22, 2008, Djupesland.
U.S. Appl. No. 12/298,292, filed Oct. 23, 2008, Djupesland.
U.S. Appl. No. 12/303,667, filed Dec. 5, 2008, Djupesland.
U.S. Appl. No. 12/375,115, filed Jan. 26, 2009, Djupesland.
U.S. Appl. No. 12/516,399, filed May 27, 2009, Djupesland.
U.S. Appl. No. 12/516,401, filed May 27, 2009, Djupesland.
U.S. Appl. No. 12/516,404, filed May 27, 2009, Djupesland.

* cited by examiner

NASAL DEVICES

This application is a national phase of International Application No. PCT/IB03/02305 filed Apr. 25, 2003 and published in the English language.

The present invention relates to a nasal delivery device for and a method of delivering substance, in particular one of a liquid, as a suspension or solution, or a powder containing a medicament, especially systemic or topical pharmaceuticals, or a vaccine to the nasal airway of a subject.

Referring to FIG. 1, the nasal airway 1 comprises the two nasal cavities 2, 3 separated by the nasal septum 4, which airway 1 includes numerous ostia, such as the paranasal sinus ostia 5 connected to the paranasal sinuses 6 and the tubal ostia 7 connected to the tuba auditiva 8 and the middle ears 9, and olfactory cells, and is lined by the nasal mucosa. The nasal airway 1 can communicate with the nasopharynx, the oral cavity and the lower airway, with the nasal airway 1 being in selective communication with the anterior region of the nasopharynx and the oral cavity by opening and closing of the oropharyngeal velum.

There are many nasal conditions which require treatment. One such condition is nasal inflammation, specifically rhinitis, which can be allergic or non-allergic and is often associated with infection and prevents normal nasal function. By way of example, allergic and non-allergic inflammation of the nasal airway can typically effect between 10 and 20% of the population, with nasal congestion of the erectile tissues of the nasal concha, lacrimation, secretion of watery mucus, sneezing and itching being the most common symptoms. As will be understood, nasal congestion impedes nasal breathing and promotes oral breathing, leading to snoring and sleep disturbance. Other nasal conditions include nasal polyps which arise from the paranasal sinuses, hypertrophic adenoids, secretory otitis media, sinus disease and reduced olfaction.

In the treatment of certain nasal conditions, the topical administration of medicaments is preferable, particularly where the nasal mucosa is the prime pathological pathway, such as in treating or relieving nasal congestion. Medicaments that are commonly topically delivered include decongestants, anti-histamines, cromoglycates, steroids and antibiotics. At present, among the known anti-inflammatory pharmaceuticals, topical steroids have been shown to have an effect on nasal congestion. Topical decongestants have also been suggested for use in relieving nasal congestion. The treatment of hypertrophic adenoids and chronic secretory otitis media using topical decongestants, steroids and anti-microbial agents, although somewhat controversial, has also been proposed. Further, the topical administration of pharmaceuticals has been used to treat or at least relieve symptoms of inflammation in the anterior region of the nasopharynx, the paranasal sinuses and the auditory tubes.

Medicaments can also be systemically delivered through the nasal pathway, the nasal pathway offering a good administration route for the systemic delivery of pharmaceuticals, such as hormones, for example, oxytocin and calcitionin, and analgetics, such as anti-migraine compositions, as the high blood flow and large surface area of the nasal mucosa advantageously provides for rapid systemic uptake.

Nasal delivery is also expected to be advantageous for the administration of medicaments requiring a rapid onset of action, for example, analgetics, anti-emetics, insulin, anti-epileptics, sedatives and hypnotica, and also other pharmaceuticals, for example, cardio-vascular drugs. It is envisaged that nasal administration will provide for a fast onset of action, at a rate similar to that of injection and at a rate much faster than that of oral administration. Indeed, for the treatment of many acute conditions, nasal administration is advantageous over oral administration, since gastric stasis can further slow the onset of action following oral administration.

It is also expected that nasal delivery could provide an effective delivery route for the administration of proteins and peptides as produced by modern biotechnological techniques. For such substances, the metabolism in the intestines and the first-pass-effect in the liver represent significant obstacles for reliable and cost-efficient delivery.

Furthermore, it is expected that nasal delivery using the nasal delivery technique of the present invention will prove effective in the treatment of many common neurological diseases, such as Alzheimer's, Parkinson's, psychiatric diseases and intracerebral infections, where not possible using existing techniques. The nasal delivery technique of the present invention allows for delivery to the olfactory region, which region is located in the superior region of the nasal cavities and represents the only region where it is possible to circumvent the blood-to-brain barrier (BBB) and enable communication with the cerebrospinal fluid (CSF) and the brain.

Also, it is expected that the nasal delivery technique of the present invention will allow for the effective delivery of vaccines.

Aside from the delivery of medicaments and vaccines, the irrigation of the nasal mucosa with liquids, in particular saline solutions, is commonly practised to remove particles and secretions, as well as to improve the mucociliary activity of the nasal mucosa These solutions can be used in combination with active pharmaceuticals.

For any kind of drug delivery, accurate and reliable dosing is essential, but it is of particular importance in relation to the administration of potent drugs which have a narrow therapeutic window, drugs with potentially serious adverse effects and drugs for the treatment of serious and life-threatening conditions. For some conditions, it is essential to individualize the dosage to the particular situation, for example, in the case of diabetes mellitus. For diabetes, and, indeed, for many other conditions, the dosage of the pharmaceutical is preferably based on actual real-time measurements. Currently, blood samples are most frequently used, but the analysis of molecules in the exhalation breath of subjects has been proposed as an alternative to blood analysis for several conditions. Breath analysis is currently used for the diagnosis of conditions such as helicobacter pylori infections which cause gastric ulcers.

WO-A-00/51672 discloses a delivery device for delivering substance, in particular a medicament, in a bi-directional flow through the nasal cavities, that is, an air flow which passes into one nostril, around the posterior margin of the nasal septum and in the opposite direction out of the other nostril. This bi-directional air flow advantageously acts to stimulate the sensory nerves in the nasal mucosa, thereby conditioning the subject for the delivery and providing a more comfortable delivery situation.

There are many kinds of existing delivery units which are capable of delivering an aerosol spray of substance as required for nasal delivery. Such delivery units include aerosol canisters as used in pressurized metered dose inhalers (pMDIs) and mechanical delivery pumps, such as liquid spray pumps.

These delivery units are well-developed, but, for the purposes of nasal delivery, suffer from the particular disadvantages of not providing aerosol sprays which have an optimized particle size distribution and the particles of the aerosol sprays being projected from the delivery nozzle with a delivery force which is such as not to allow for the aerosol spray to be readily entrained in a gas flow. Indeed, the delivery forces are such that the particles of the aerosol spray would impact, and collect, on any proximate surfaces.

In the field of inhalation technology, spacers have been developed as a means of overcoming the particular problem caused by the speed of the particles of delivered aerosol sprays. Spacers are essentially chambers into which an aerosol spray is delivered and from which a subject inhales.

It is an aim of the present invention to provide an improved nasal delivery device for and a method of delivering substance to the nasal airway of a subject.

In one aspect the present invention provides a nasal delivery device for delivering substance to a nasal airway of a subject, comprising: a nosepiece for fitting to a nostril of a subject; a delivery unit comprising a substance supply unit and a nozzle unit including at least one nozzle fluidly connected to the substance supply unit for generating an aerosol spray for delivery to a nasal airway of the subject; and an aerosol interactor operable to interact with an aerosol spray as generated by the at least one nozzle.

Preferably, the aerosol interactor is configured such that operation thereof is actuated prior to actuation of the delivery unit.

Preferably, the at least one nozzle is configured such as to deliver the aerosol spray towards the nosepiece.

In one embodiment the aerosol interactor comprises a flow director for directing an interacting gas flow at the aerosol spray such as to interact with the same.

Preferably, the flow director includes at least one flow-directing channel downstream of the at least one nozzle for directing an interacting gas flow and delivering at least one interacting gas stream to interact with the aerosol spray.

More preferably, the at least one flow-directing channel has an annular outlet disposed about a delivery path of the aerosol spray.

In one embodiment the at least one flow-directing channel is configured such as to direct the at least one interacting gas stream substantially orthogonally to the delivery path of the aerosol spray.

In another embodiment the at least one flow-directing channel is configured such as to direct the at least one interacting gas stream in a direction inclined to the delivery path of the aerosol spray and away from the nosepiece.

Preferably, the at least one flow-directing channel is an annular, frusto-conical channel configured to deliver a conical, annular interacting gas stream to the delivery path of the aerosol spray.

More preferably, the at least one flow-directing channel is configured such that an apex of the conical, annular interacting gas stream delivered thereby is co-incident with the delivery path of the aerosol spray.

In one embodiment the delivery device further comprises: a chamber in fluid communication with the nosepiece; and wherein the flow director includes an annular flow channel for providing an annular gas flow over an inner periphery of the chamber.

Preferably, the chamber includes a flow deflector disposed at the inner periphery thereof and downstream of the at least one nozzle which is such as to obstruct the annular gas flow generated at the inner periphery of the chamber and cause the same to be deflected inwardly and generate a turbulent zone downstream of the at least one nozzle.

More preferably, the flow deflector comprises an annular member.

Preferably, the flow director includes a plurality of flow-directing channels in spaced relation downstream of the at least one nozzle for directing an interacting gas flow and delivering a plurality of interacting gas streams to interact with the aerosol spray.

Preferably, the delivery device further comprises: a mouthpiece through which the subject in use exhales.

In one embodiment the mouthpiece is fluidly connected to the flow director such that at least part of the exhaled air flow provides the interacting gas flow.

In another embodiment the delivery device further comprises: a gas supply unit for delivering a gas flow, the gas supply unit being fluidly connected to the flow director such that at least part of the delivered gas flow provides the interacting gas flow.

In another embodiment the aerosol interactor comprises a movable element disposed downstream of the at least one nozzle.

Preferably, the aerosol interactor is disposed in opposed relation to the at least one nozzle.

More preferably, the aerosol interactor is configured such as to present a continuous surface to the aerosol spray.

Preferably, the aerosol interactor is disposed relative to the at least one nozzle such that the aerosol spray is reflected thereby.

In one embodiment the movable element comprises a rotatable element.

In another embodiment the movable element comprises first and second rotatable elements coupled so as to rotate in unison, the first rotatable element including vanes oriented in one sense such as to be rotated in one sense by a gas flow thereover, and the second rotatable element being disposed downstream of the at least one nozzle and including vanes oriented in the other, opposite sense to the vanes of the first rotatable element such as to generate an interacting gas flow in an upstream direction towards the at least one nozzle on being rotated in the one sense by rotation of the first rotatable element.

Preferably, the first rotatable element is disposed upstream of the at least one nozzle.

In a further embodiment the nozzle unit includes a tubular element which extends downstream of the at least one nozzle and includes a plurality of apertures for providing a plurality of flow paths therethrough, and the aerosol interactor comprises a rotatable element disposed at a downstream end of the tubular element, the rotatable element including first, outer vanes oriented in one sense and disposed radially beyond the tubular element such that the rotatable element is rotated in one sense by a gas flow thereover, and second, inner vanes oriented in the other, opposite sense to the outer vanes such as to generate an interacting gas flow in an upstream direction towards the at least one nozzle with rotation of the rotatable element, which interacting gas flow is such as to interact with the aerosol spray and pass through the apertures in the tubular element.

In one embodiment the substance supply unit comprises an aerosol canister.

In another embodiment the substance supply unit comprises a delivery pump.

Preferably, the delivery pump comprises a liquid spray pump.

In another aspect the present invention provides a method of delivering substance to a nasal airway of a subject, comprising the steps of: fitting a nosepiece to a nostril of a subject; actuating a delivery unit to generate an aerosol spray from at least one nozzle for delivery to a nasal airway of the subject; and operating an aerosol interactor to interact with an aerosol spray as generated by the at least one nozzle.

Preferably, operation of the aerosol interactor is actuated prior to actuation of the delivery unit.

Preferably, the aerosol spray is delivered towards the nosepiece.

In one embodiment the aerosol interactor comprises a flow director, and the step of operating the aerosol interactor comprises the step of: directing an interacting gas flow at the aerosol spray such as to interact with the same.

Preferably, the flow director includes at least one flow-directing channel downstream of the at least one nozzle, and the step of operating the aerosol interactor comprises the step of: directing an interacting gas flow to deliver at least one interacting gas stream to interact with the aerosol spray.

More preferably, the at least one flow-directing channel has an annular outlet disposed about a delivery path of the aerosol spray.

In one embodiment the at least one interacting gas stream is directed substantially orthogonally to the delivery path of the aerosol spray.

In another embodiment the at least one interacting gas stream is directed in a direction inclined to the delivery path of the aerosol spray and away from the nosepiece.

Preferably, the at least one interacting gas stream is a conical, annular interacting gas stream.

More preferably, an apex of the conical, annular interacting gas stream is co-incident with the delivery path of the aerosol spray.

In one embodiment the aerosol spray is delivered into a chamber in fluid communication with the nosepiece; and further comprising the step of providing an annular gas flow over an inner periphery of the chamber.

Preferably, the chamber includes a flow deflector disposed at the inner periphery thereof and downstream of the at least one nozzle; and further comprising the step of: obstructing the annular gas flow generated at the inner periphery of the chamber such as to cause the same to be deflected inwardly and generate a turbulent zone downstream of the at least one nozzle.

More preferably, the flow deflector comprises an annular member.

Preferably, the flow director includes a plurality of flow-directing channels in spaced relation downstream of the at least one nozzle; and the step of operating the aerosol interactor comprises the step of: directing an interacting gas flow to deliver a plurality of interacting gas streams to interact with the aerosol spray.

Preferably, the method further comprises the step of: the subject exhaling through a mouthpiece.

In one embodiment the mouthpiece is fluidly connected to the flow director such that at least part of the exhaled air flow provides the interacting gas flow.

In another embodiment the method further comprises the step of: supplying a gas flow from a gas supply unit, at least part of the supplied gas flow being delivered to the flow director as the interacting gas flow.

In another embodiment the aerosol interactor comprises a movable element disposed downstream of the at least one nozzle; and the step of operating the aerosol interactor comprises the step of: moving the movable element downstream of the at least one nozzle such as to interact with the aerosol spray.

Preferably, the aerosol interactor is disposed in opposed relation to the at least one nozzle.

More preferably, the aerosol interactor is configured such as to present a continuous surface to the aerosol spray.

Preferably, the aerosol interactor is disposed relative to the at least one nozzle such that the aerosol spray is reflected thereby.

In one embodiment the movable element comprises a rotatable element.

In another embodiment the movable element comprises first and second rotatable elements coupled so as to rotate in unison, the first rotatable element including vanes oriented in one sense such as to be rotated in one sense by a gas flow thereover, and the second rotatable element being disposed downstream of the at least one nozzle and including vanes oriented in the other, opposite sense to the vanes of the first rotatable element such as to generate an interacting gas flow in an upstream direction towards the at least one nozzle on being rotated in the one sense by rotation of the first rotatable element; and further comprising the step of: driving a gas flow over the first rotatable element such as to cause rotation of the same and thereby rotate the second rotatable element such as to generate an interacting gas flow in an upstream direction towards the at least one nozzle.

Preferably, the first rotatable element is disposed upstream of the at least one nozzle.

In a further embodiment the step of actuating the delivery unit to generate an aerosol spray comprises the step of: actuating the delivery unit to generate an aerosol spray from at least one nozzle into a tubular element which extends downstream of the at least one nozzle, the tubular element including a plurality of apertures for providing a plurality of flow paths therethrough; the step of operating the aerosol interactor comprises the step of: moving a rotatable element disposed at a downstream end of the tubular element, the rotatable element including first, outer vanes oriented in one sense and disposed radially beyond the tubular element such that the rotatable element is rotated in one sense by a gas flow thereover, and second, inner vanes oriented in the other, opposite sense to the outer vanes such as to generate an interacting gas flow in an upstream direction towards the at least one nozzle with rotation of the rotatable element; and further comprising the step of: driving a gas flow over the outer vanes of the rotatable element to cause rotation of the same and thereby cause the inner vanes of the rotatable element to generate an interacting gas flow in an upstream direction towards the at least one nozzle, which interacting gas flow is such as to interact with the aerosol spray and pass through the apertures in the tubular element.

In one embodiment the aerosol spray is from an aerosol canister.

In another embodiment the aerosol spray is from a delivery pump.

Preferably, the delivery pump comprises a liquid spray pump.

Preferred embodiments of the present invention will now be described hereinbelow by way of example only with reference to the accompanying drawings, in which:

FIG. 1 schematically illustrates the nasal airway of a human subject;

Figure 1:
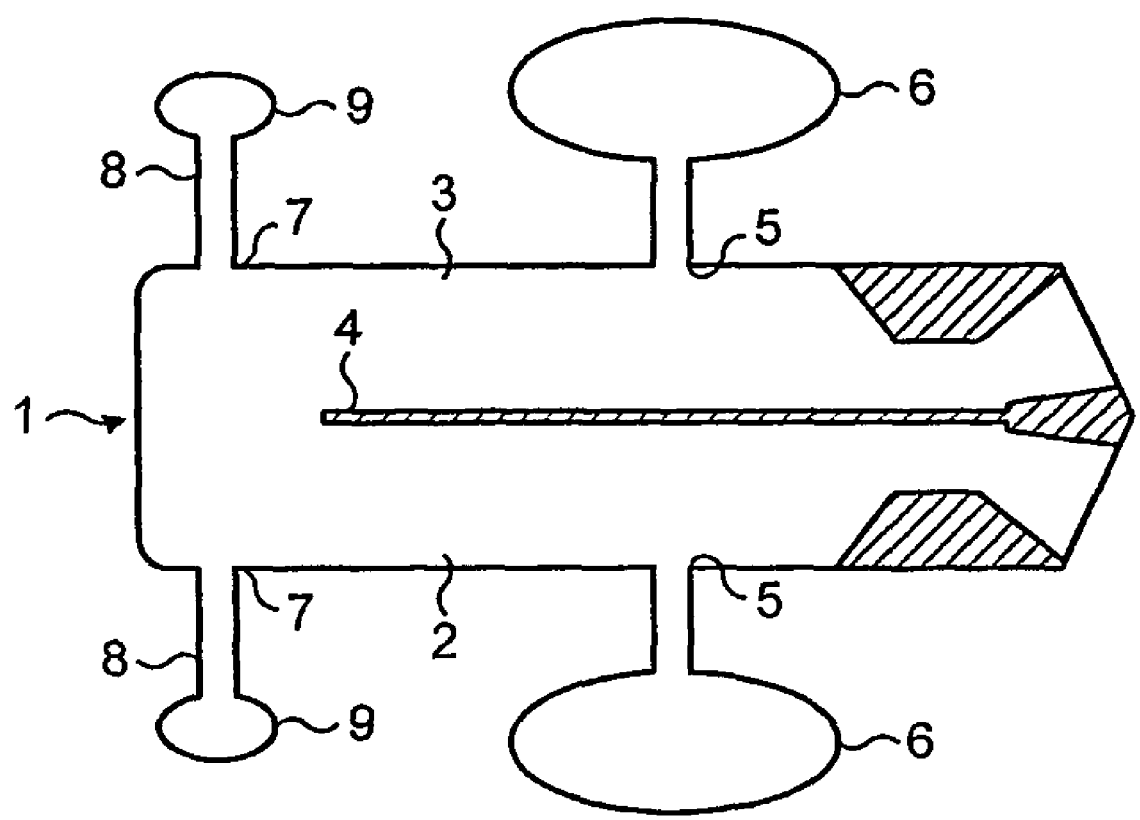
Figure 2A:
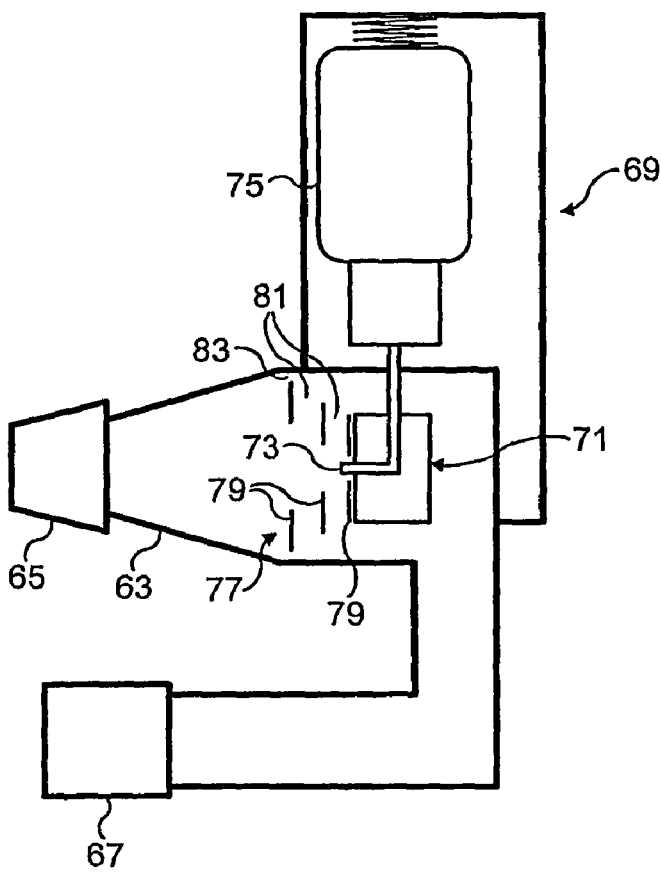
FIG. 2(a) illustrates a nasal delivery device in accordance with a first embodiment of the present invention.
Figure 2B:
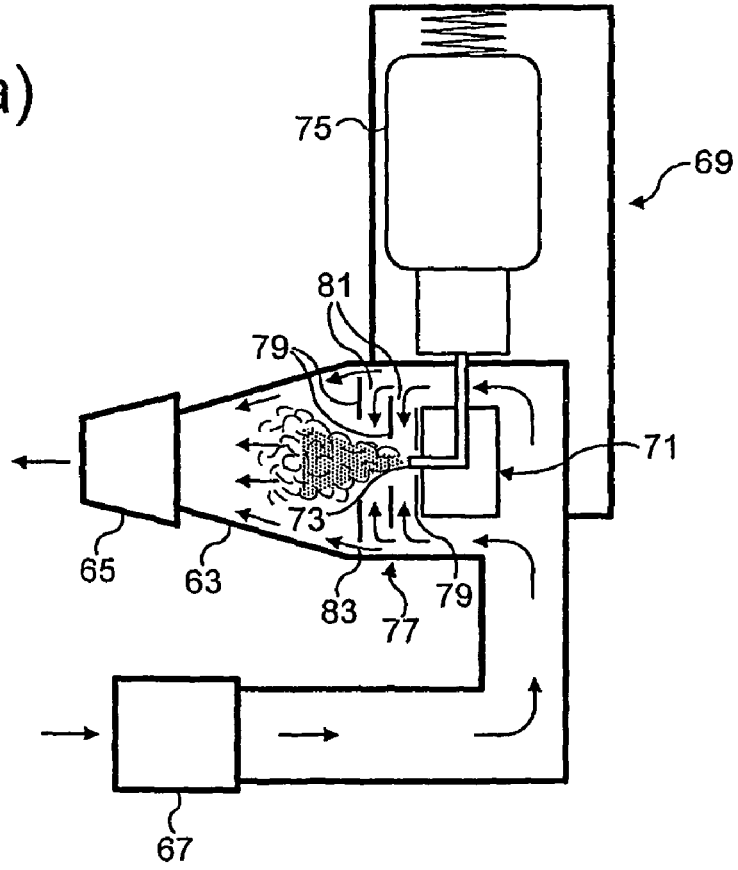
FIG. 2(b) illustrates the nasal delivery device of FIG. 2(a) in the actuated configuration.

FIGS. 2(a) and (b) illustrate a nasal delivery device in accordance with a first embodiment of the present invention.

The delivery device comprises a chamber 63, in this embodiment a substantially tubular member, into which an aerosol spray is delivered, a nosepiece 65 for fitting to a nostril of a subject which is in fluid communication with the chamber 63 and disposed to one, the downstream, end of the chamber 63, and a mouthpiece 67 through which the subject exhales and which is in fluid communication with the chamber 63.

The delivery device further comprises a delivery unit 69, in this embodiment a breath-actuated unit, for delivering an aerosol spray of substance into the chamber 63. The delivery unit 69 comprises a nozzle unit 71 which includes a nozzle 73 for delivering an aerosol spray of substance, and a substance supply unit 75 for delivering a metered dose of substance to the nozzle unit 71.

In this embodiment the nozzle 73 of the nozzle unit 71 is directed towards the nosepiece 65 and is disposed so as to be co-axial therewith.

In this embodiment the substance supply unit 75 is an aerosol canister for delivering a metered volume of a propellant, preferably a hydrofluoroalkane (HFA) propellant or the like, containing substance, typically a medicament, either as a suspension or solution.

In an alternative embodiment the substance supply unit 75 could comprise a mechanical delivery pump, in particular a liquid delivery pump or a powder delivery pump, which delivers metered doses of substance on actuation thereof.

The delivery unit 69 is primeable, in this embodiment by loading a biasing element, and includes a release mechanism, which, when triggered, releases the biasing element and actuates the substance supply unit 75 to deliver a metered dose of substance.

The delivery device further comprises a flow director 77 which is configured to direct at least part of a delivered gas flow, in this embodiment an exhaled air flow, through the chamber 63 such as to interact with an aerosol spray as generated from the nozzle 73 of the nozzle unit 71 on actuation of the substance supply unit 75, whereby an aerosol spray, when delivered from the nozzle 73, is acted upon by the directed air flow such as to optimize characteristics of the particles thereof, and in particular modify the particle size distribution of the particles of the aerosol spray and decelerate the particles of the aerosol spray, which particles, once so optimized, are then entrained by the air flow through the chamber 63.

The flow director 77 comprises at least one baffle 79, in this embodiment a plurality of baffles 79, which defines at least one flow-directing channel 81 forwardly of the nozzle 73 of the nozzle unit 71, in this embodiment a plurality of flow-directing channels 81 in spaced relation forwardly of the nozzle 73 of the nozzle unit 71, for directing part of the exhaled air flow as at least one interacting air stream, in this embodiment a plurality of interacting air streams, to interact with an aerosol spray as generated from the nozzle 73 of the nozzle unit 71.

In this embodiment the at least one flow-directing channel 81 has an annular outlet and is configured such as to direct the at least one interacting air stream substantially orthogonally to the direction of delivery of the aerosol spray as generated from the nozzle 73 of the nozzle unit 71.

In this embodiment the at least one baffle 79 is configured such as to define an annular flow channel 83 at the inner periphery of the chamber 63, which annular channel 83 is such that the other part of the exhaled air flow provides an annular air flow over the inner periphery of the chamber 63.

With this configuration, each interacting air stream in effect provides an air zone, akin to an air wall, through which an aerosol spray as generated from the nozzle 73 of the nozzle unit 71 has to penetrate.

Operation of the delivery device will now be described hereinbelow.

Firstly, the nosepiece 65 is fitted to a nostril of a subject and the mouthpiece 67 is gripped in the lips of the subject.

The subject then begins to exhale through the mouthpiece 67, which exhalation acts to close the oropharyngeal velum of the subject and deliver an air flow through the chamber 63 and the nasal airway 1 of the subject, part of which air flow is directed through the at least one flow-directing channel 81 and delivered as at least one interacting air stream radially to the delivery path of an aerosol spray as generated from the nozzle 73 of the nozzle unit 71 and the other part of which air flow flows through the annular flow channel 83 and provides an annular air flow over the inner periphery of the chamber 63.

When a predetermined flow rate is achieved through the chamber 63, the substance supply unit 75 is actuated to deliver a metered dose of substance through the nozzle 73 of the nozzle unit 71, which nozzle 73 generates an aerosol spray in a direction towards the nosepiece 65. The aerosol spray, when delivered from the nozzle 73, is acted upon by the at least one interacting air flow such as to optimize characteristics of the particles of the aerosol spray, which particles, as so optimized, are then entrained by the air flow through the chamber 63.

In this way, the particles of the generated aerosol spray as delivered to the nasal airway 1 have optimized characteristics, and in particular a modified particle size distribution and a much reduced velocity. Optimizing the particle size distribution of the aerosol spray provides for improved delivery to targeted sites in the nasal airway. In decelerating the particles of the aerosol spray, deposition on unwanted surfaces, which would result where the particles are delivered directly from the nozzle 73 of the nozzle unit 71 without intervention, is avoided.

Figure 3A:
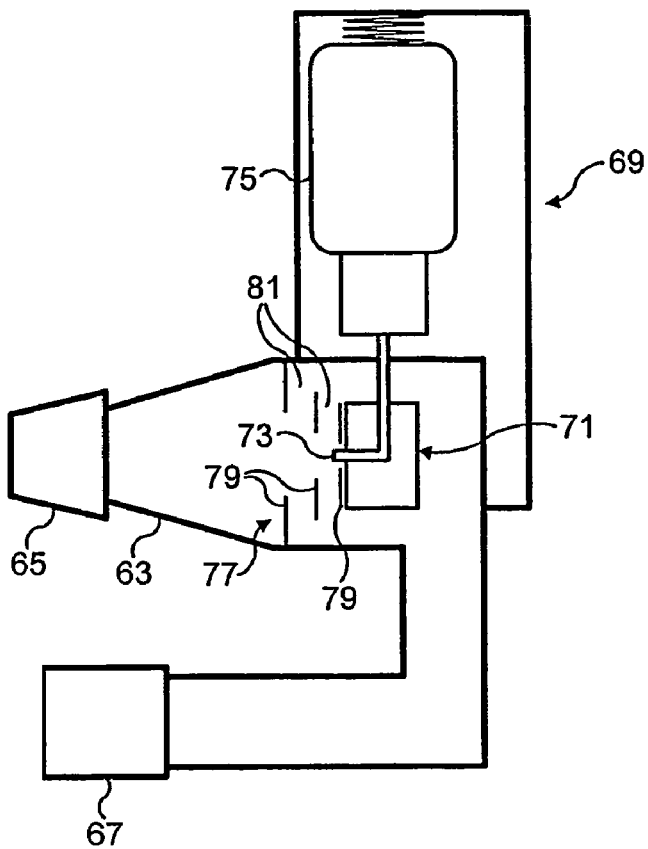
FIG. 3(a) illustrates a nasal delivery device in accordance with a second embodiment of the present invention.
Figure 3B:
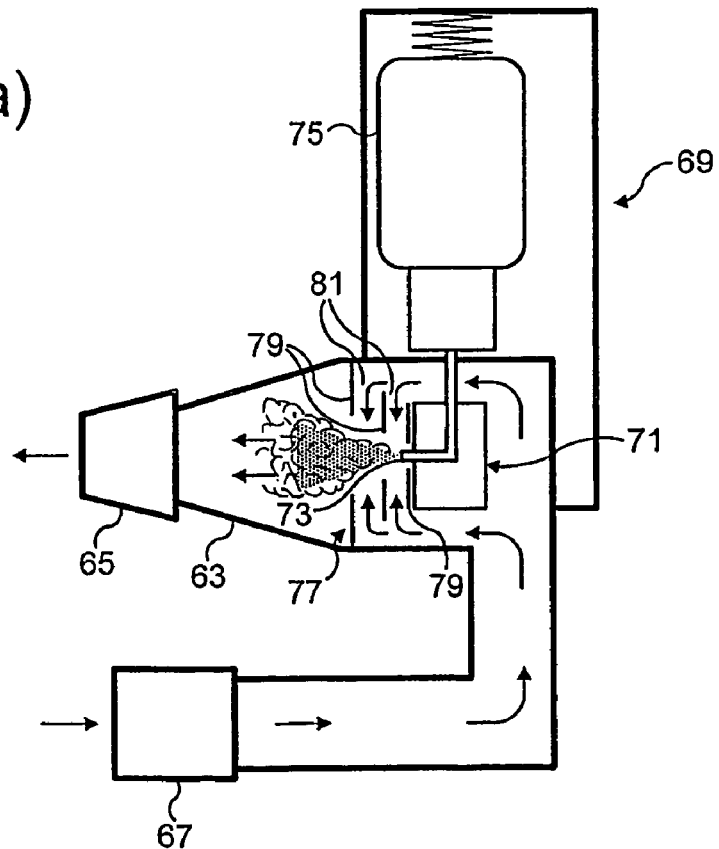
FIG. 3(b) illustrates the nasal delivery device of FIG. 3(a) in the actuated configuration.

FIGS. 3(*a*) and (*b*) illustrate a nasal delivery device in accordance with a second embodiment of the present invention.

The delivery device of this embodiment is very similar to the delivery device of the above-described first embodiment, and thus, in order to avoid unnecessary duplication of description, only the differences will be described in detail, with like reference signs designating like parts.

The delivery device of this embodiment differs from that of the above-described first embodiment in that the flow director 77 is modified to omit the annular flow channel 83, whereby the entire exhaled air flow is directed through the at least one flow-directing channel 81.

Operation of the delivery device is the same as for the above-described first embodiment, with the entire exhaled air flow being delivered to the chamber 63, and hence the nasal airway 1, in response to exhalation through the mouthpiece 67.

Figure 4A:
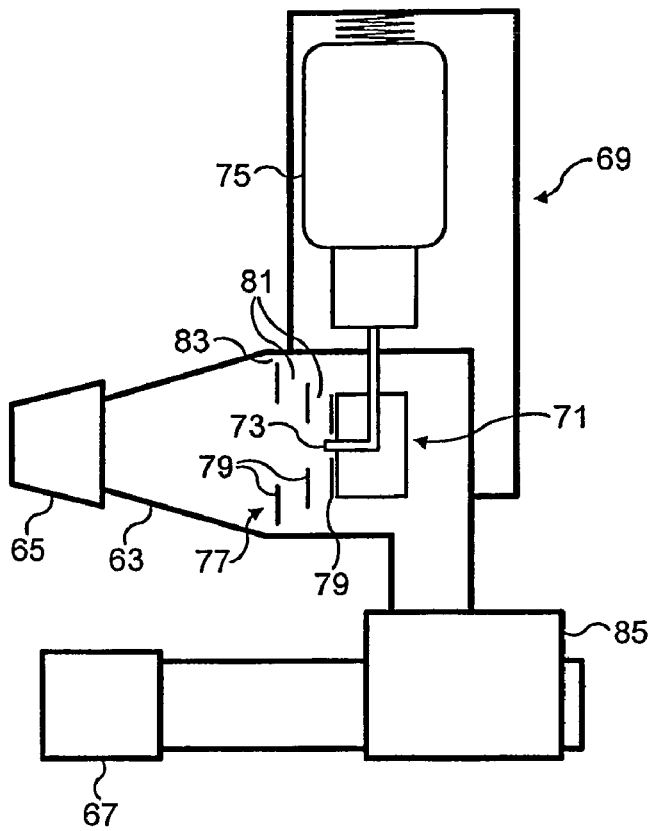
FIG. 4(a) illustrates a nasal delivery device in accordance with a third embodiment of the present invention.
Figure 4B:
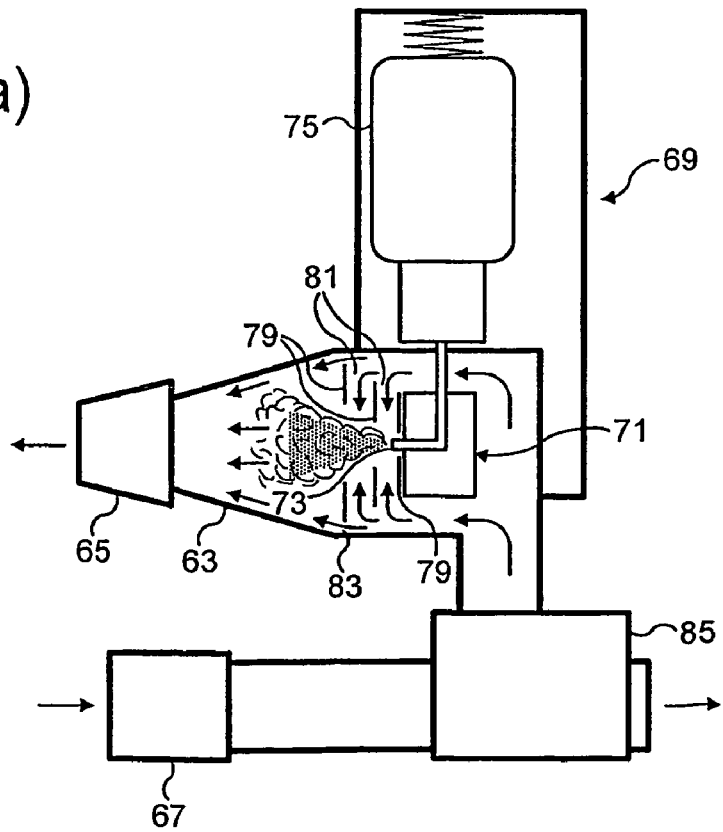
FIG. 4(b) illustrates the nasal delivery device of FIG. 4(a) in the actuated configuration.

FIGS. 4(*a*) and (*b*) illustrate a nasal delivery device in accordance with a third embodiment of the present invention.

The delivery device of this embodiment is very similar to the delivery device of the above-described first embodiment, and thus, in order to avoid unnecessary duplication of description, only the differences will be described in detail, with like reference signs designating like parts.

The delivery device of this embodiment differs from that of the above-described first embodiment in further comprising an exhalation breath actuatable gas supply unit 85 for delivering a gas flow to the chamber 63 in response to exhalation by a subject, and in that the mouthpiece 67 is in fluid communication with the gas supply unit 85 and not the chamber 63, whereby a gas flow is delivered to the chamber 63, and hence the nasal airway 1, in response to exhalation through the mouthpiece 67.

Operation of the delivery device is the same as for the above-described first embodiment, with a gas flow being delivered to the chamber 63, and hence the nasal airway 1, in response to exhalation through the mouthpiece 67.

Figure 5A:
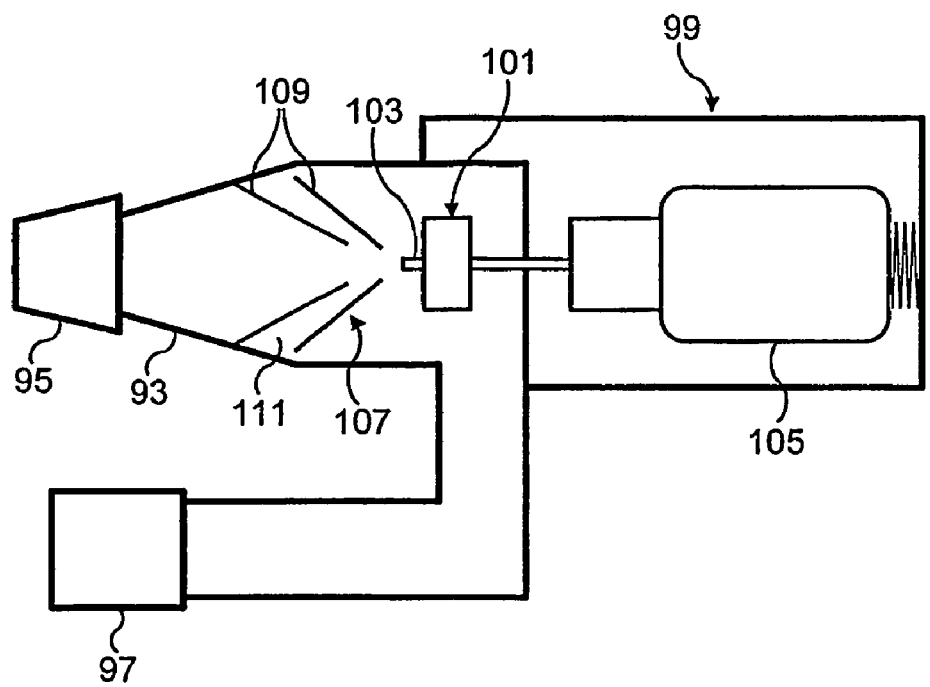
FIG. 5(a) illustrates a nasal delivery device in accordance with a fourth embodiment of the present invention.
Figure 5B:
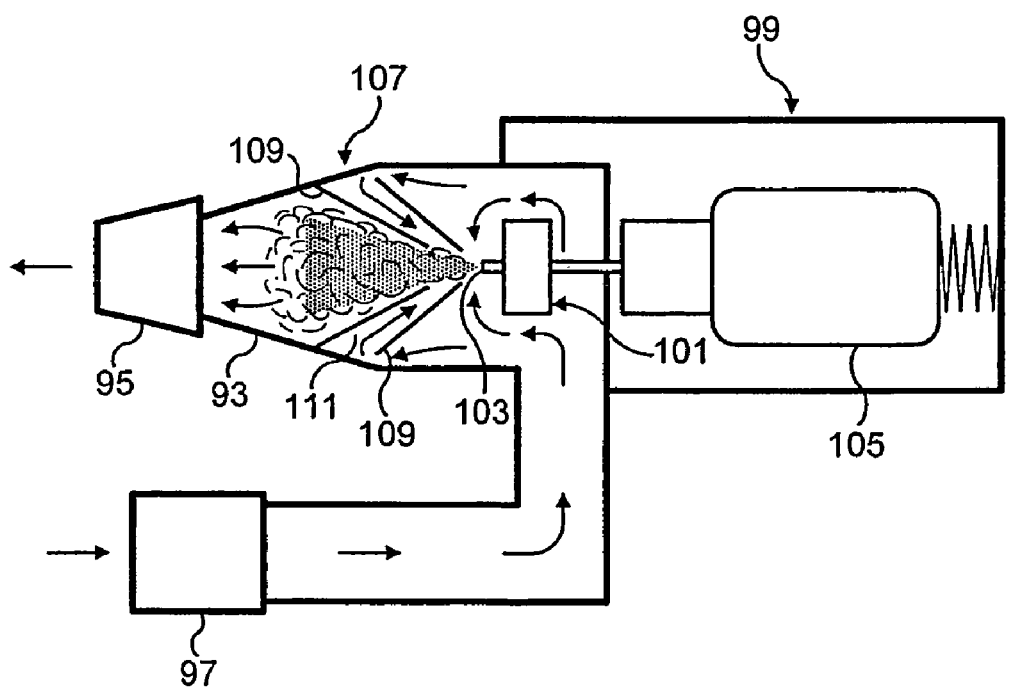
FIG. 5(b) illustrates the nasal delivery device of FIG. 5(a) in the actuated configuration.

FIGS. 5(*a*) and (*b*) illustrate a nasal delivery device in accordance with a fourth embodiment of the present invention.

The delivery device comprises a chamber 93, in this embodiment a substantially tubular member, into which an aerosol spray is delivered, a nosepiece 95 for fitting to a nostril of a subject which is in fluid communication with the chamber 93 and disposed to one, the downstream, end of the chamber 93, and a mouthpiece 97 through which the subject exhales and which is in fluid communication with the chamber 93.

The delivery device further comprises a delivery unit 99, in this embodiment a breath-actuated unit, for delivering an aerosol spray of substance into the chamber 93. The delivery unit 99 comprises a nozzle unit 101 which includes a nozzle 103 for delivering an aerosol spray of substance, and a substance supply unit 105 for delivering a metered dose of substance to the nozzle unit 101.

In this embodiment the nozzle 103 of the nozzle unit 101 is directed towards the nosepiece 95 and is disposed so as to be co-axial therewith.

In this embodiment the substance supply unit 105 is an aerosol canister for delivering a metered volume of a propellant, preferably a hydrofluoroalkane (HFA) propellant or the like, containing substance, typically a medicament, either as a suspension or solution.

In an alternative embodiment the substance supply unit 105 could comprise a mechanical delivery pump, in particular a liquid delivery pump or a powder delivery pump, which delivers metered doses of substance on actuation thereof.

The delivery unit 99 is primeable, in this embodiment by loading a biasing element, and includes a release mechanism, which, when triggered, releases the biasing element and actuates the substance supply unit 105 to deliver a metered dose of substance.

The delivery device further comprises a flow director 107 which is configured to direct a delivered gas flow, in this embodiment an exhaled air flow, through the chamber 93 such as to interact with an aerosol spray as generated from the nozzle 103 of the nozzle unit 101 on actuation of the substance supply unit 105, whereby an aerosol spray, when delivered from the nozzle 103, is acted upon by the directed air flow such as to optimize characteristics of the particles thereof, and in particular modify the particle size distribution of the particles of the aerosol spray and decelerate the particles of the aerosol spray, which particles, once so optimized, are then entrained by the air flow through the chamber 93.

The flow director 107 comprises at least one baffle 109, in this embodiment a plurality of baffles 109, which defines at least one flow-directing channel 111 forwardly of the nozzle 103 of the nozzle unit 101, in this embodiment a single flow-directing channel 111, for directing at least part of the exhaled air flow as at least one interacting air stream, in this embodiment a single interacting air stream, to interact with an aerosol spray as generated from the nozzle 103 of the nozzle unit 101.

In this embodiment the at least one flow-directing channel 111 has an annular outlet and is configured such as to direct the at least one interacting air stream in a direction inclined to the direction of delivery of an aerosol spray as generated from the nozzle 103 of the nozzle unit 101 and away from the nosepiece 95.

In this embodiment the at least one flow-directing channel 111 is an annular, frusto-conical channel, here of narrowing section towards the outlet thereof, which delivers a conical, annular interacting air stream to the delivery path of an aerosol spray as generated from the nozzle 103 of the nozzle unit 101. In this embodiment the apex of the conical, annular interacting air stream is co-incident with the delivery path of an aerosol spray as generated from the nozzle 103 of the nozzle unit 101.

With this configuration, the interacting air stream in effect provides an air zone, akin to an air wall, through which an aerosol spray as generated from the nozzle 103 of the nozzle unit 101 has to penetrate.

Operation of the delivery device will now be described hereinbelow.

Firstly, the nosepiece 95 is fitted to a nostril of a subject and the mouthpiece 97 is gripped in the lips of the subject.

The subject then begins to exhale through the mouthpiece 97, which exhalation acts to close the oropharyngeal velum of the subject and deliver an air flow through the chamber 93 and the nasal airway 1 of the subject, which air flow is directed through the at least one flow-directing channel 111 and delivered as at least one conical, annular interacting air stream to the delivery path of an aerosol spray as generated from the nozzle 103 of the nozzle unit 101.

When a predetermined flow rate is achieved through the chamber 93, the substance supply unit 105 is actuated to deliver a metered dose of substance through the nozzle 103 of the nozzle unit 101, which nozzle 103 generates an aerosol spray in a direction towards the nosepiece 95. The aerosol spray, when delivered from the nozzle 103, is acted upon by the at least one interacting gas stream such as to optimize characteristics of the particles of the aerosol spray, which particles, as so optimized, are then entrained by the air flow through the chamber 93.

In this way, the particles of the generated aerosol spray as delivered to the nasal airway 1 have optimized characteristics, and in particular a modified particle size distribution and a much reduced velocity. Optimizing the particle size distribution of the aerosol spray provides for improved delivery to targeted sites in the nasal airway. In decelerating the particles of the aerosol spray, deposition on unwanted surfaces, which would result where the particles are delivered directly from the nozzle 103 of the nozzle unit 101 without intervention, is avoided.

Figure 6A:
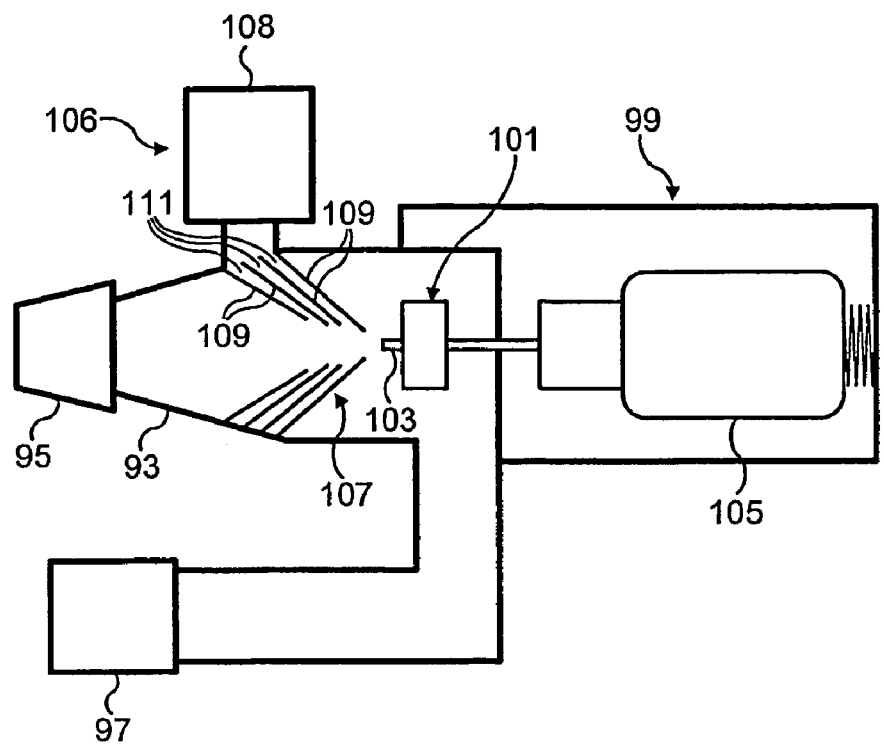
FIG. 6(a) illustrates a nasal delivery device in accordance with a fifth embodiment of the present invention.
Figure 6B:
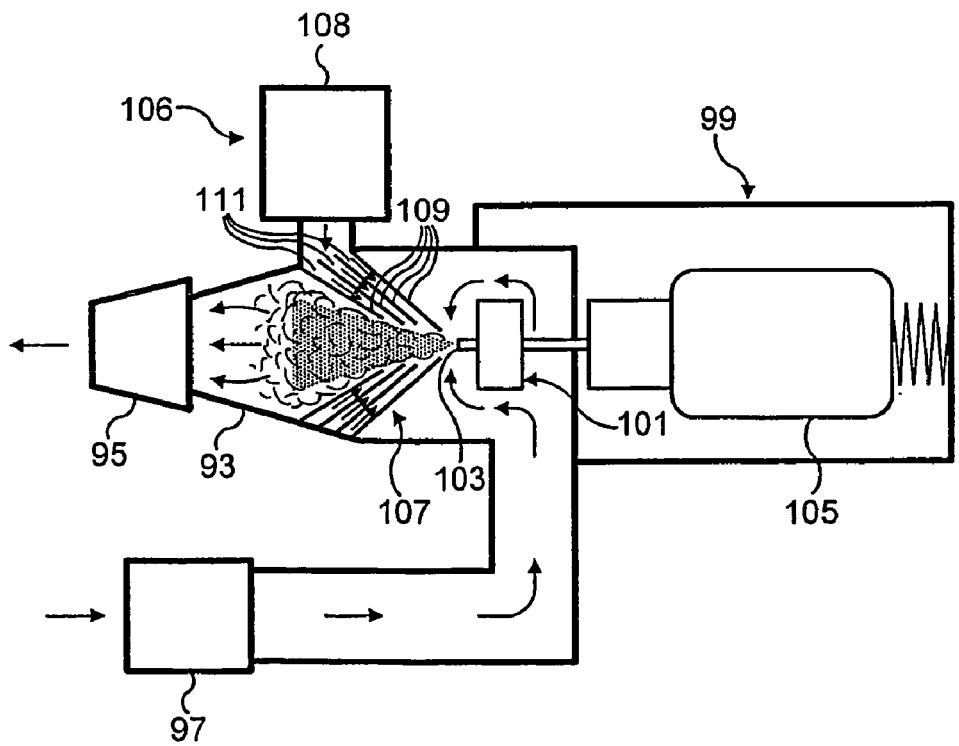
FIG. 6(b) illustrates the nasal delivery device of FIG. 6(a) in the actuated configuration.

FIGS. 6(*a*) and (*b*) illustrate a nasal delivery device in accordance with a fifth embodiment of the present invention.

The delivery device comprises a chamber 93, in this embodiment a substantially tubular member, into which an aerosol spray is delivered, a nosepiece 95 for fitting to a nostril of a subject which is in fluid communication with the chamber 93 and disposed to one, the downstream, end of the chamber 93, and a mouthpiece 97 through which the subject exhales and which is in fluid communication with the chamber 93.

The delivery device further comprises a delivery unit 99, in this embodiment a breath-actuated unit, for delivering an aerosol spray of substance into the chamber 93. The delivery unit 99 comprises a nozzle unit 101 which includes a nozzle 103 for delivering an aerosol spray of substance, and a substance supply unit 105 for delivering a metered dose of substance to the nozzle unit 101.

In this embodiment the nozzle 103 of the nozzle unit 101 is directed towards the nosepiece 95 and disposed so as to be co-axial therewith.

In this embodiment the substance supply unit 105 is an aerosol canister for delivering a metered volume of a propellant, preferably a hydrofluoroalkane (HFA) propellant or the like, containing substance, typically a medicament, either as a suspension or solution.

In an alternative embodiment the substance supply unit 105 could comprise a mechanical delivery pump, in particular a liquid delivery pump or a powder delivery pump, which delivers metered doses of substance on actuation thereof.

The delivery unit 99 is primeable, in this embodiment by loading a biasing element, and includes a release mechanism, which, when triggered, releases the biasing element and actuates the substance supply unit 105 to deliver a metered dose of substance.

The delivery device further comprises a flow director unit 106 for directing an interacting gas flow, separate to the exhalation breath of a subject, into the chamber 93 such as to interact with an aerosol spray as generated from the nozzle 103 of the nozzle unit 101 on actuation of the substance supply unit 105, whereby an aerosol spray, when delivered from the nozzle 103, is acted upon by the directed gas flow such as to optimize characteristics of the particles thereof, which particles, once so optimized, are then entrained by a gas flow, in this embodiment the exhalation air flow, through the chamber 93.

The flow director unit 106 comprises a flow director 107 which is configured to direct an interacting gas flow to the delivery path of an aerosol spray as generated from the nozzle 103 of the nozzle unit 101 on actuation of the substance supply unit 105, and a gas supply unit 108 which is actuatable to deliver a gas flow to the flow director 107.

In this embodiment the flow director 107 comprises a plurality of baffles 109 which define a plurality of flow-directing channels 111 in spaced relation forwardly of the nozzle 103 of the nozzle unit 101 for directing a plurality of interacting gas streams to the delivery path of an aerosol spray as generated from the nozzle 103 of the nozzle unit 101 on actuation of the substance supply unit 105.

In this embodiment the flow-directing channels 111 each have an annular outlet and are configured such as to direct an interacting gas stream in a direction inclined to the direction of delivery of an aerosol spray as generated from the nozzle 103 of the nozzle unit 101 and away from the nosepiece 95.

In this embodiment the flow-directing channels 111 are annular, frusto-conical channels, each of narrowing section towards the respective outlets thereof, which deliver conical, annular interacting gas streams to the delivery path of an aerosol spray as generated from the nozzle 103 of the nozzle unit 101. In this embodiment the apexes of the conical, annular interacting gas streams are co-incident with the delivery path of an aerosol spray as generated from the nozzle 103 of the nozzle unit 101.

With this configuration, the interacting gas streams each in effect provide a gas zone, akin to a gas wall, through which an aerosol spray as generated from the nozzle 103 of the nozzle unit 101 has to penetrate.

Operation of the delivery device will now be described hereinbelow.

Firstly, the nosepiece 95 is fitted to a nostril of a subject and the mouthpiece 97 is gripped in the lips of the subject.

The subject then begins to exhale through the mouthpiece 97, which exhalation acts to close the oropharyngeal velum of the subject and deliver an air flow through the chamber 93 and the nasal airway 1 of the subject, which air flow acts to actuate the gas supply unit 108 to deliver an interacting gas flow to the flow-directing channels 111, which interacting gas flow is directed through the flow-directing channels 111 and delivered as conical, annular interacting gas streams to the delivery path of an aerosol spray as generated from the nozzle 103 of the nozzle unit 101.

When a predetermined flow rate is achieved through the chamber 93, the substance supply unit 105 is actuated to deliver a metered dose of substance through the nozzle 103 of the nozzle unit 101, which nozzle 103 generates an aerosol spray in a direction towards the nosepiece 95. The aerosol spray, when delivered from the nozzle 103, is acted upon by the interacting gas streams in succession such as to optimize characteristics of particles of the aerosol spray, which particles, as so optimized, are then entrained by the air flow through the chamber 93.

In this way, the particles of the generated aerosol spray as delivered to the nasal airway 1 have optimized characteristics, and in particular a modified particle size distribution and a much reduced velocity. Optimizing the particle size distribution of the aerosol spray provides for improved delivery to targeted sites in the nasal airway. In decelerating the particles of the aerosol spray, deposition on unwanted surfaces, which would result where the particles are delivered directly from the nozzle 103 of the nozzle unit 101 without intervention, is avoided.

Figure 7A:
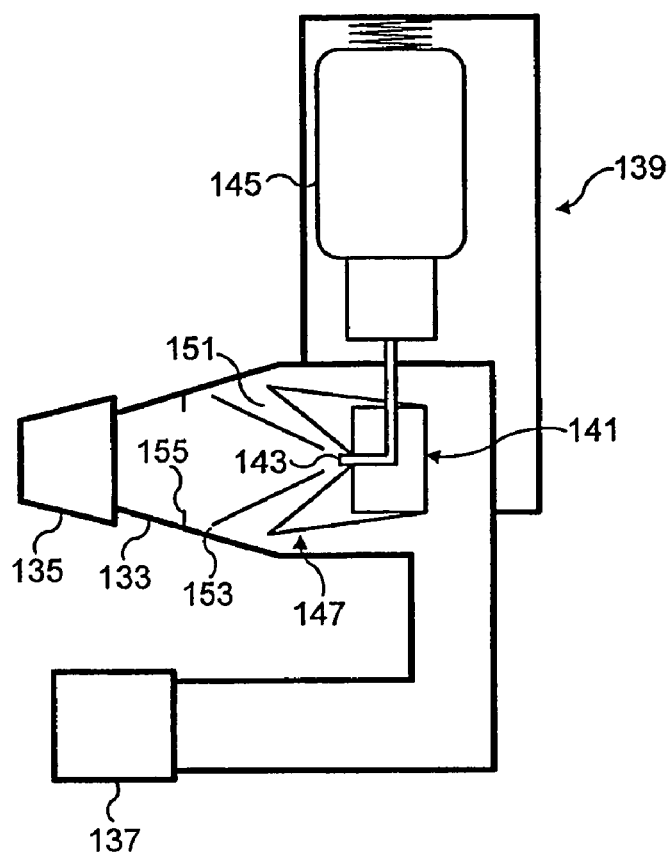
FIG. 7(a) illustrates a nasal delivery device in accordance with a sixth embodiment of the present invention.
Figure 7B:
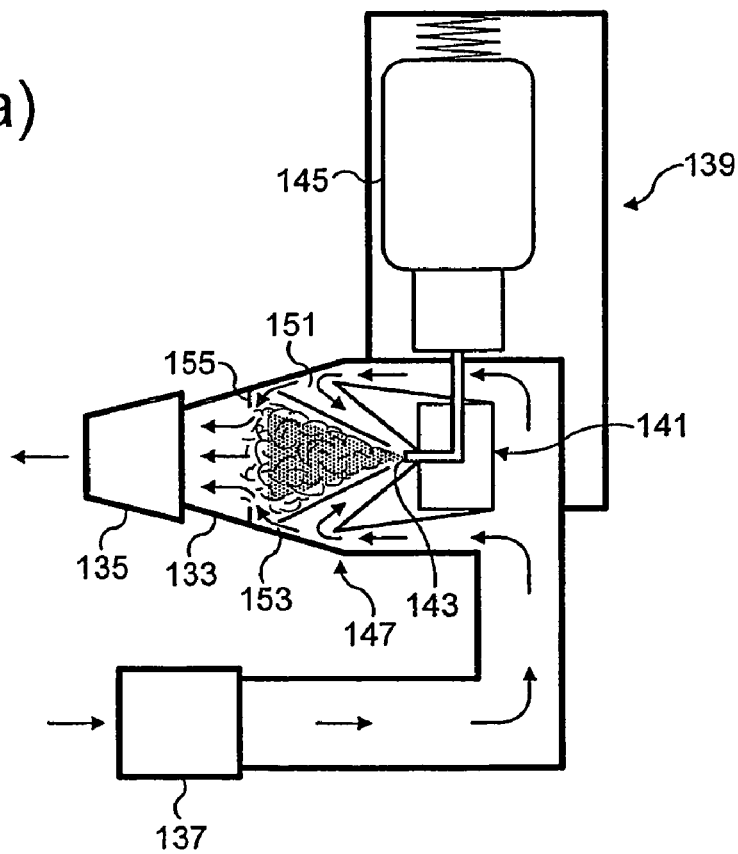
FIG. 7(b) illustrates the nasal delivery device of FIG. 7(a) in the actuated configuration.

FIGS. 7(a) and (b) illustrate a nasal delivery device in accordance with a sixth embodiment of the present invention.

The delivery device comprises a chamber 133, in this embodiment a substantially tubular member, into which an aerosol spray is delivered, a nosepiece 135 for fitting to a nostril of a subject which is in fluid communication with the chamber 133 and disposed to one, the downstream, end of the chamber 133, and a mouthpiece 137 through which the subject exhales and which is in fluid communication with the chamber 133.

The delivery device further comprises a delivery unit 139, in this embodiment a breath-actuated unit, for delivering an aerosol spray of substance into the chamber 133. The delivery unit 139 comprises a nozzle unit 141 which includes a nozzle 143 for delivering an aerosol spray of substance, and a substance supply unit 145 for delivering a metered dose of substance to the nozzle unit 141.

In this embodiment the nozzle 143 of the nozzle unit 141 is directed towards the nosepiece 135 and disposed so as to be co-axial therewith.

In this embodiment the substance supply unit 145 is an aerosol canister for delivering a metered volume of a propellant, preferably a hydrofluoroalkane (HFA) propellant or the like, containing substance, typically a medicament, either as a suspension or solution.

In an alternative embodiment the substance supply unit 145 could comprise a mechanical delivery pump, in particular a liquid delivery pump or a powder delivery pump, which delivers metered doses of substance on actuation thereof.

The delivery unit 139 is primeable, in this embodiment by loading a biasing element, and includes a release mechanism, which, when triggered, releases the biasing element and actuates the substance supply unit 145 to deliver a metered dose of substance.

The delivery device further comprises a flow director 147 which is configured to direct part of a delivered gas flow, in this embodiment an exhaled air flow, through the chamber 133 such as to interact with an aerosol spray as generated from the nozzle 143 of the nozzle unit 141 on actuation of the substance supply unit 145, whereby an aerosol spray, when delivered from the nozzle 143, is acted upon by the directed air flow such as to optimize characteristics of the particles thereof, and in particular modify the particle size distribution of the aerosol spray and decelerate the particles of the aerosol spray, which particles, once so optimized, are then entrained by the air flow through the chamber 133.

The flow director 147 includes at least one flow-directing channel 151, in this embodiment a single flow-directing channel 151, for directing part of the delivered air flow to interact with an aerosol spray as generated from the nozzle 143 of the nozzle unit 141. In an alternative embodiment the flow director 147 could include a plurality of flow-directing channels 151.

In this embodiment the at least one flow-directing channel 151 has an annular outlet and is configured such as to direct the at least one interacting air stream in a direction inclined to the direction of delivery of an aerosol spray as generated from the nozzle 143 of the nozzle unit 141 and away from the nosepiece 135.

In this embodiment the at least one flow-directing channel 151 is an annular, frusto-conical channel, here of narrowing section towards the outlet thereof, which delivers a conical, annular interacting air stream to the delivery path of an aerosol spray as generated from the nozzle 143 of the nozzle unit 141. In this embodiment the apex of the conical, annular interacting air stream is co-incident with the delivery path of an aerosol spray as generated from the nozzle 143 of the nozzle unit 141.

With this configuration, the interacting air stream in effect provides an air zone, akin to an air wall, through which an aerosol spray as generated from the nozzle 143 of the nozzle unit 141 has to penetrate.

In this embodiment the nozzle 143 of the nozzle unit 141 is shielded such that the interacting air flow is provided entirely by the at least one interacting air stream which is delivered through the at least one flow-directing channel 151.

In this embodiment the flow director 147 further includes an annular flow channel 153 at the inner periphery of the chamber 133, which annular channel 153 is such that the other part of the delivered air flow provides an annular air flow over the inner periphery of the chamber 133.

In this embodiment the chamber 133 includes a flow deflector 155, here an annular member, disposed about the inner periphery thereof downstream of the nozzle 143 of the nozzle unit 141, which flow deflector 155 is located such as to obstruct the annular air flow generated at the inner periphery of the chamber 133 and cause the annular air flow to be deflected inwardly and generate a turbulent zone ahead of the nozzle 143 which further interacts with the aerosol spray as generated.

Operation of the delivery device will now be described hereinbelow.

Firstly, the nosepiece 135 is fitted to a nostril of a subject and the mouthpiece 137 is gripped in the lips of the subject.

The subject then begins to exhale through the mouthpiece 137, which exhalation acts to close the oropharyngeal velum of the subject and deliver an air flow through the chamber 133 and the nasal airway 1 of the subject, part of which air flow is directed through the at least one flow-directing channel 151 and delivered as at least one interacting air stream to the delivery path of an aerosol spray as generated from the nozzle 143 of the nozzle unit 141, in this embodiment towards the root of the aerosol spray, and the other part of which air flow flows through the annular flow channel 153 and provides an annular air flow over the inner periphery of the chamber 133.

When a predetermined flow rate is achieved through the chamber 133, the substance supply unit 145 is actuated to deliver a metered dose of substance through the nozzle 143 of the nozzle unit 141, which nozzle 143 generates an aerosol spray in a direction towards the nosepiece 135. The aerosol spray, when delivered from the nozzle 143, is acted upon by the at least one interacting air stream such as to optimize characteristics of the particles of the aerosol spray, which particles, as so optimized, are then entrained by the air flow through the chamber 133.

In this way, the particles of the generated aerosol spray as delivered to the nasal airway 1 have optimized characteristics, and in particular a modified particle size distribution and a much reduced velocity. Optimizing the particle size distribution of the aerosol spray provides for improved delivery to targeted sites in the nasal airway. In decelerating the particles of the aerosol spray, deposition on unwanted surfaces, which would result where the particles are delivered directly from the nozzle 143 of the nozzle unit 141 without intervention, is avoided.

Figure 8A:
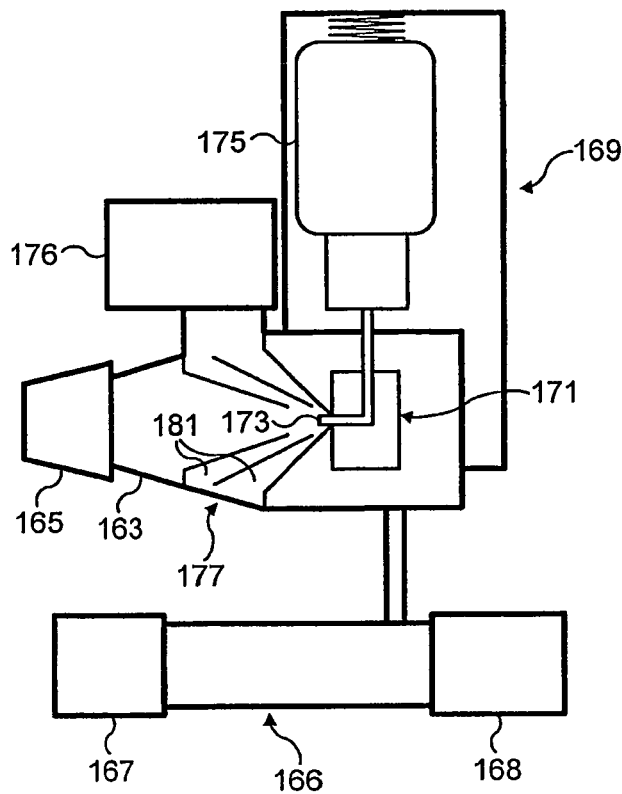
FIG. 8(a) illustrates a nasal delivery device in accordance with a seventh embodiment of the present invention.
Figure 8B:
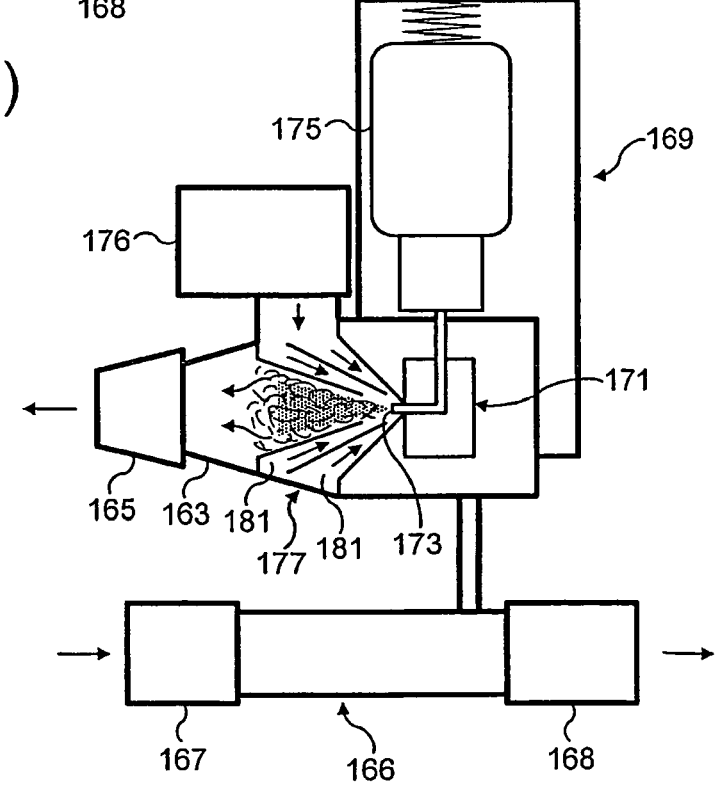
FIG. 8(b) illustrates the nasal delivery device of FIG. 8(a) in the actuated configuration.

FIGS. 8(a) and (b) illustrate a nasal delivery device in accordance with a seventh embodiment of the present invention.

The delivery device comprises a chamber 163, in this embodiment a substantially tubular member, into which an aerosol spray is delivered, a nosepiece 165 for fitting to a nostril of a subject which is in fluid communication with the chamber 163 and disposed to one, the downstream, end of the chamber 163, and a mouthpiece unit 166. In this embodiment the delivery device is configured such as to provide no fluid communication path between the mouthpiece unit 166 and the chamber 163.

The mouthpiece unit 166 includes a mouthpiece 167 which is gripped by the lips of the subject, and an exhalation breath sensor 168 which is fluidly connected to the mouthpiece 167, in this embodiment for detecting the flow rate of the oral exhalation breath through the mouthpiece unit 166. In an alternative embodiment the exhalation breath sensor 168 can be configured to detect a pressure developed in the mouthpiece unit 166. In another alternative embodiment the exhalation breath sensor 168 can be configured to detect both the flow rate of the oral exhalation breath and the pressure developed in the mouthpiece unit 166.

The delivery device further comprises a delivery unit 169 for delivering an aerosol spray of substance into the chamber 163. The delivery unit 169 comprises a nozzle unit 171 which includes a nozzle 173 for delivering an aerosol spray of substance, and a substance supply unit 175 for delivering a metered dose of substance to the nozzle unit 171.

In this embodiment the nozzle 173 of the nozzle unit 171 is directed towards the nosepiece 165 and disposed so as to be co-axial therewith.

In this embodiment the substance supply unit 175 is an aerosol canister for delivering a metered volume of a propellant, preferably a hydrofluoroalkane (HFA) propellant or the like, containing substance, typically a medicament, either as a suspension or solution.

In an alternative embodiment the substance supply unit 175 could comprise a mechanical delivery pump, in particular a liquid delivery pump or a powder delivery pump, which delivers metered doses of substance on actuation thereof.

The delivery unit 169 is primeable, in this embodiment by loading a biasing element, and includes a release mechanism, which, when triggered, releases the biasing element and actuates the substance supply unit 175 to deliver a metered dose of substance.

The delivery device further comprises a gas supply unit 176 which is actuatable to deliver a gas flow to the chamber 163, as will be described in more detail hereinbelow.

The delivery device further comprises a flow director 177 which is fluidly connected to the gas supply unit 176 for directing an interacting gas flow, separate to the exhalation breath of a subject, into the chamber 163 such as to interact with an aerosol spray as generated from the nozzle 173 of the nozzle unit 171 on actuation of the substance supply unit 175, whereby an aerosol spray, when delivered from the nozzle 173, is acted upon by the interacting gas flow such as to optimize characteristics of the particles thereof, and in particular modify the particle size distribution of the particles of the aerosol spray and decelerate the particles of the aerosol spray, which particles, once so optimized, are then entrained through the chamber 163.

In this embodiment the flow director 177 includes a plurality of flow-directing channels 181 in spaced relation forwardly of the nozzle 173 of the nozzle unit 171 for directing the delivered gas flow as a plurality of interacting gas streams to the delivery path of an aerosol spray as generated from the nozzle 173 of the nozzle unit 171 on actuation of the substance supply unit 175.

In this embodiment the flow-directing channels 181 each have an annular outlet and are configured such as to direct an interacting gas stream in a direction inclined to the direction of delivery of an aerosol spray as generated from the nozzle 173 of the nozzle unit 171 and away from the nosepiece 165.

In this embodiment the flow-directing channels 181 are annular, frusto-conical channels, each of narrowing section towards the respective outlets thereof, which deliver conical, annular interacting gas streams to the delivery path of an aerosol spray as generated from the nozzle 173 of the nozzle unit 171. In this embodiment the apexes of the conical, annular interacting gas streams are co-incident with the delivery path of an aerosol spray as generated from the nozzle 173 of the nozzle unit 171.

With this configuration, the interacting gas streams each in effect provide a gas zone, akin to a gas wall, through which an aerosol spray as generated from the nozzle 173 of the nozzle unit 171 has to penetrate.

Operation of the delivery device will now be described hereinbelow.

Firstly, the nosepiece 165 is fitted to a nostril of a subject and the mouthpiece 167 is gripped in the lips of the subject.

The subject then begins to exhale through the mouthpiece 167 of the mouthpiece unit 166, which exhalation acts to close the oropharyngeal velum of the subject.

On generation of one or both of a predetermined pressure and flow rate through the mouthpiece unit 166, as detected by the exhalation breath sensor 168, the gas supply unit 176 is actuated to deliver a gas flow through the chamber 163 and the nasal airway 1 of the subject, which gas flow is directed through the flow-directing channels 181 and delivered as conical, annular interacting gas streams to the delivery path of an aerosol spray as generated from the nozzle 173 of the nozzle unit 171.

In this embodiment, when a predetermined flow rate is achieved through the chamber 163, and hence the nasal airway 1, the substance supply unit 175 is actuated to deliver a metered dose of substance through the nozzle 173 of the nozzle unit 171, which nozzle 173 generates an aerosol spray in a direction towards the nosepiece 165. The aerosol spray, when delivered from the nozzle 173, is acted upon by the interacting gas streams such as to optimize characteristics of the particles of the aerosol spray, which particles, as so optimized, are then entrained by the gas flow through the chamber 163.

In alternative embodiments the substance supply unit 175 can be configured such as to be actuated in response to the generation of a predetermined pressure or both a predetermined pressure and flow rate in the chamber 163.

In this way, the particles of the generated aerosol spray as delivered to the nasal airway 1 have optimized characteristics, and in particular a modified particle size distribution and a much reduced velocity. Optimizing the particle size distribution of the aerosol spray provides for improved delivery to targeted sites in the nasal airway. In decelerating the particles of the aerosol spray, deposition on unwanted surfaces, which would result where the particles are delivered directly from the nozzle 173 of the nozzle unit 171 without intervention, is avoided.

Figure 9A:
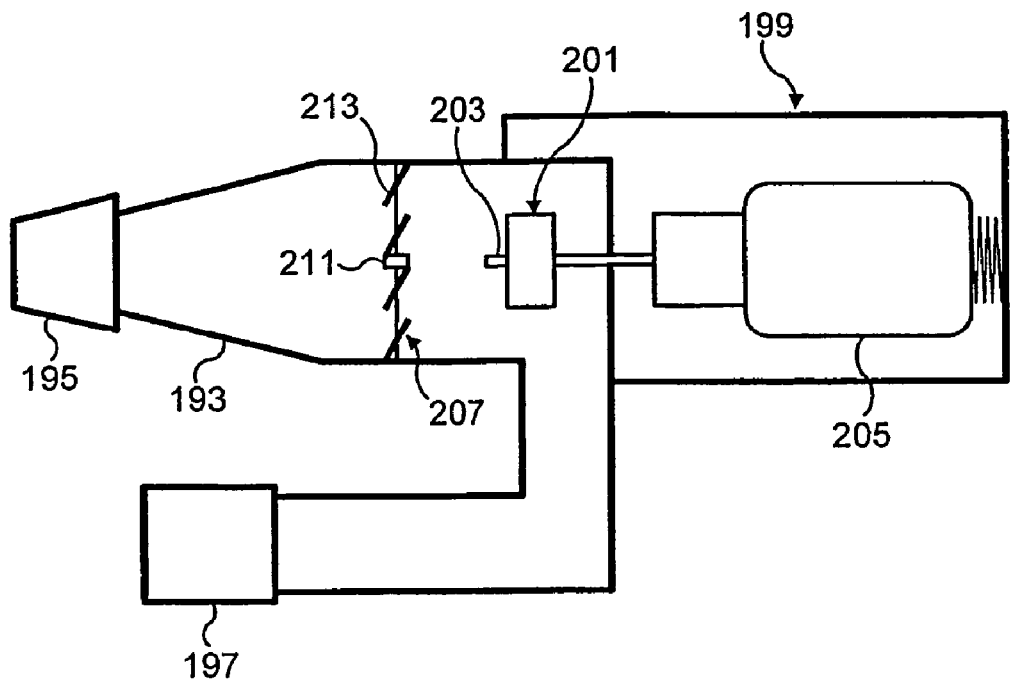
FIG. 9(a) illustrates a nasal delivery device in accordance with an eighth embodiment of the present invention.
Figure 9B:
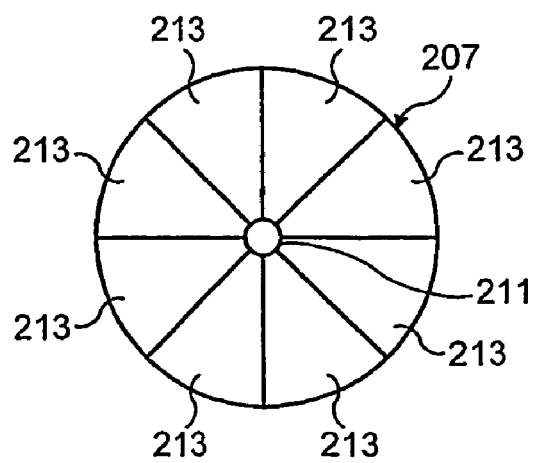
FIG. 9(b) illustrates one end view of the rotatable element of the nasal delivery device of FIG. 9(a)
Figure 9C:
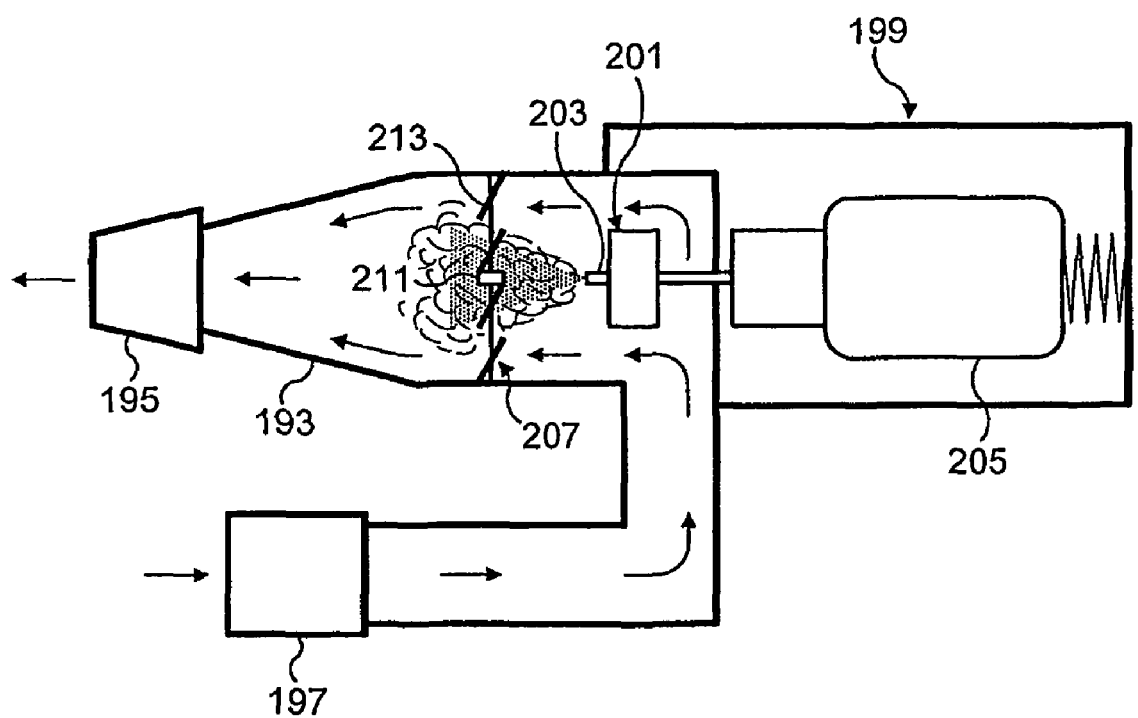
FIG. 9(c) illustrates the nasal delivery device of FIG. 9(a) in the actuated configuration.

FIGS. 9(a) to (c) illustrate a nasal delivery device in accordance with an eighth embodiment of the present invention.

The delivery device comprises a chamber 193, in this embodiment a substantially tubular member, into which an aerosol spray is delivered, a nosepiece 195 for fitting to a nostril of a subject which is in fluid communication with the chamber 193 and disposed to one, the downstream, end of the chamber 193, and a mouthpiece 197 through which the subject exhales and which is in fluid communication with the chamber 193.

The delivery device further comprises a delivery unit 199, in this embodiment a breath-actuated unit, for delivering an aerosol spray of substance into the chamber 193. The delivery unit 199 comprises a nozzle unit 201 which includes a nozzle 203 for delivering an aerosol spray of substance, and a substance supply unit 205 for delivering a metered dose of substance to the nozzle unit 201.

In this embodiment the nozzle 203 of the nozzle unit 201 is directed towards the nosepiece 195 and is disposed so as to be co-axial therewith.

In this embodiment the substance supply unit 205 is an aerosol canister for delivering a metered volume of a propellant, preferably a hydrofluoroalkane (HFA) propellant or the like, containing substance, typically a medicament, either as a suspension or solution.

In an alternative embodiment the substance supply unit 205 could comprise a mechanical delivery pump, in particular a liquid delivery pump or a powder delivery pump, which delivers metered doses of substance on actuation thereof.

The delivery unit 199 is primeable, in this embodiment by loading a biasing element, and includes a release mechanism, which, when triggered, releases the biasing element and actuates the substance supply unit 205 to deliver a metered dose of substance.

The delivery device further comprises a moving element 207 which is disposed downstream of and opposes the nozzle 203 of the nozzle unit 201 such as to interact with an aerosol spray as generated from the nozzle 203, whereby an aerosol spray, when delivered from the nozzle 203, is acted upon by the moving element 207, in this embodiment at least in part by reflection from the surface of the moving element 207, such as to optimize characteristics of the aerosol spray, and in particular modify the particle size distribution of the particles of the aerosol spray and decelerate particles of the aerosol spray, which particles, once so optimized, are then entrained by the air flow through the chamber 193.

In this embodiment the moving element 207 comprises a rotatable element which is mounted about a central pivot 211 and includes a plurality of inclined vanes 213 such as to be rotated by the action of a delivered gas flow, in this embodiment an exhaled air flow, over the vanes 213. In this embodiment the vanes 213 of the moving element 207 are configured such as to present a continuous surface to an aerosol spray as generated from the nozzle 203 of the nozzle unit 201, and thereby no direct path to the nosepiece 195.

Operation of the delivery device will now be described hereinbelow.

Firstly, the nosepiece 195 is fitted to a nostril of a subject and the mouthpiece 197 is gripped in the lips of the subject.

The subject then begins to exhale through the mouthpiece 197, which exhalation acts to close the oropharyngeal velum of the subject and deliver an air flow through the chamber 193 and the nasal airway 1 of the subject, which air flow acts to rotate the movable element 207.

When a predetermined flow rate is achieved through the chamber 193, the substance supply unit 205 is actuated to deliver a metered dose of substance through the nozzle 203 of the nozzle unit 201, which nozzle 203 generates an aerosol spray in a direction towards the nosepiece 195. The aerosol spray, when delivered from the nozzle 195, is acted upon by the movable element 207 such as to optimize characteristics of the particles of the aerosol spray, which particles, as so optimized, are then entrained by the air flow through the chamber 193.

In this way, the particles of the generated aerosol spray as delivered to the nasal airway 1 have optimized characteristics, and in particular an optimized particle size distribution and a much reduced velocity. Optimizing the particle size distribution of the aerosol spray provides for improved delivery to targeted sites in the nasal airway. In decelerating the particles of the aerosol spray, deposition on unwanted surfaces, which would result where the particles are delivered directly from the nozzle 203 of the nozzle unit 201 without intervention, is avoided.

Figure 10A:
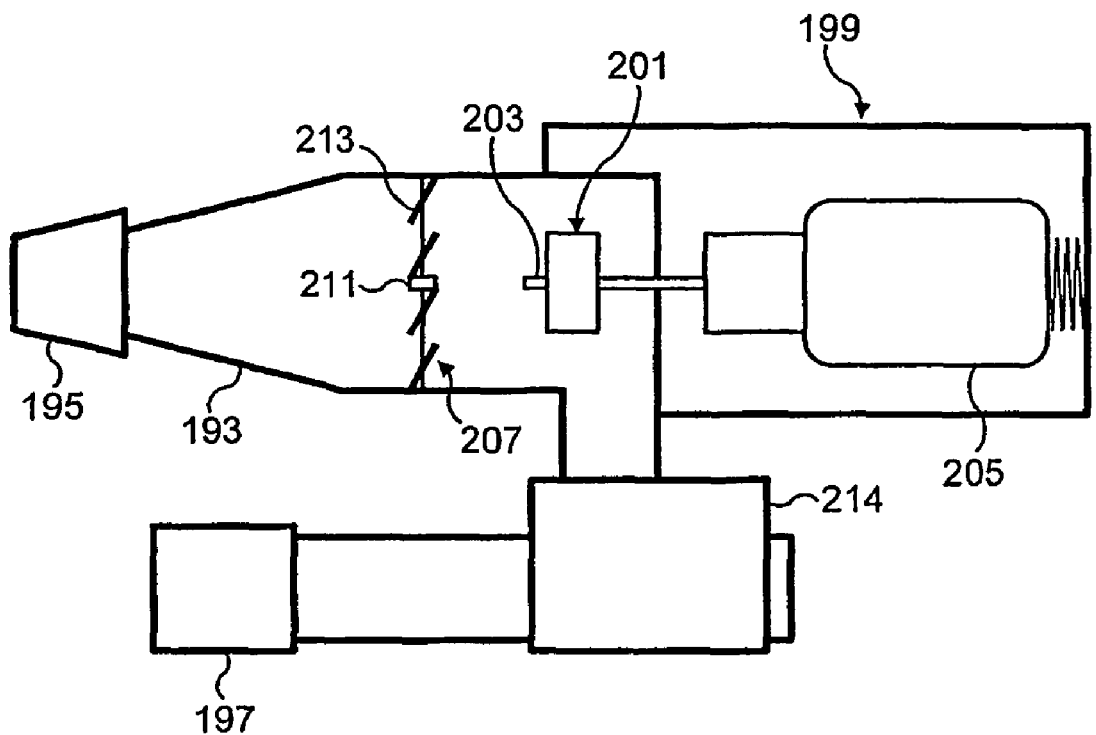
FIG. 10(a) illustrates a nasal delivery device in accordance with a ninth embodiment of the present invention.
Figure 10B:
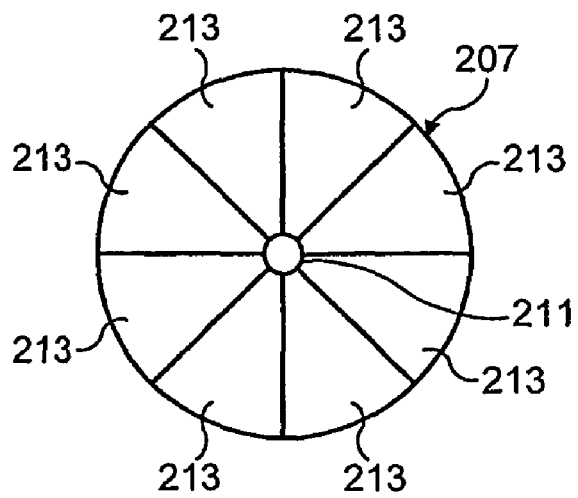
FIG. 10(b) illustrates one end view of the rotatable element of the nasal delivery device of FIG. 10(a)
Figure 10C:
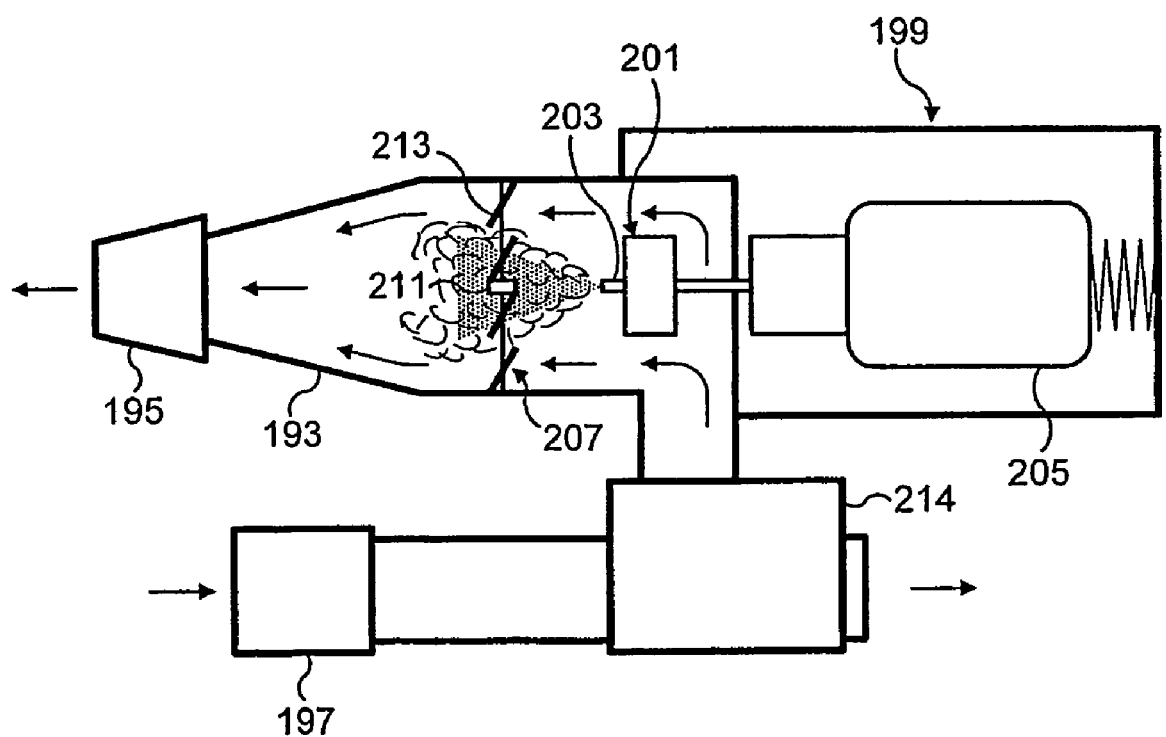
FIG. 10(c) illustrates the nasal delivery device of FIG. 10(a) in the actuated configuration.
Figure 11A:
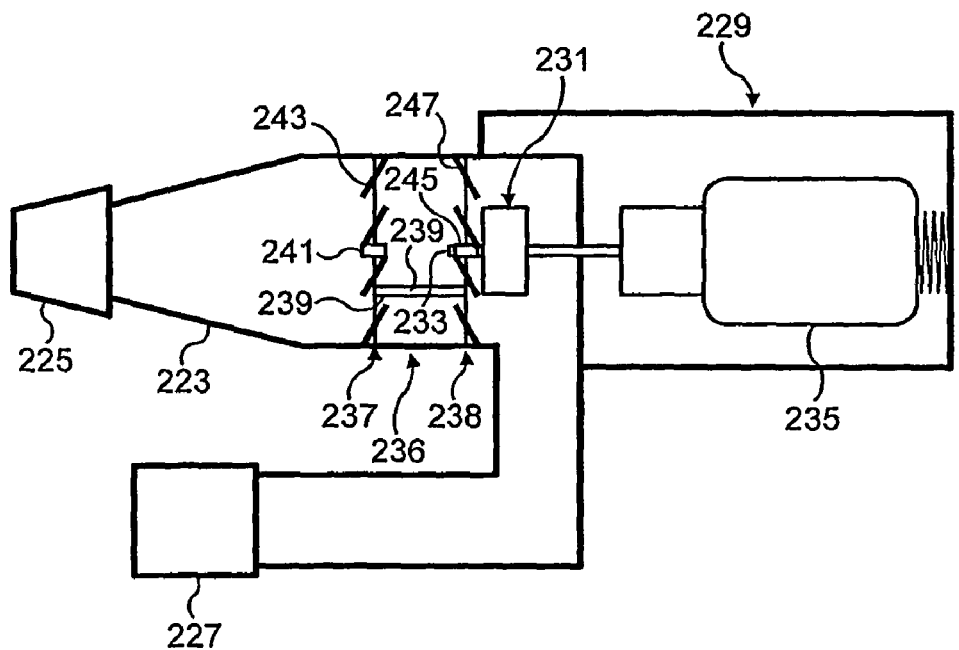
FIG. 11(a) illustrates a nasal delivery device in accordance with a tenth embodiment of the present invention.
Figure 11B:
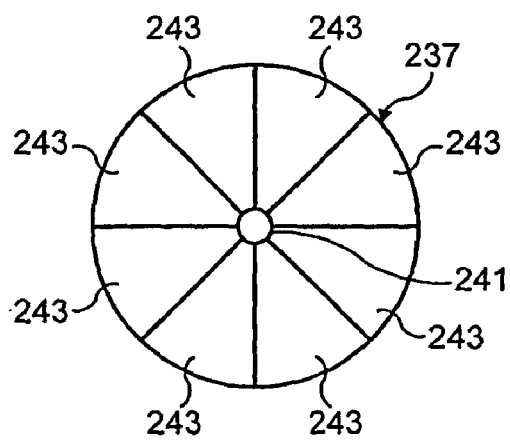
FIG. 11(b) illustrates one end view of the first rotatable element of the rotatable unit of the nasal delivery device of FIG. 11(a)
Figure 11C:
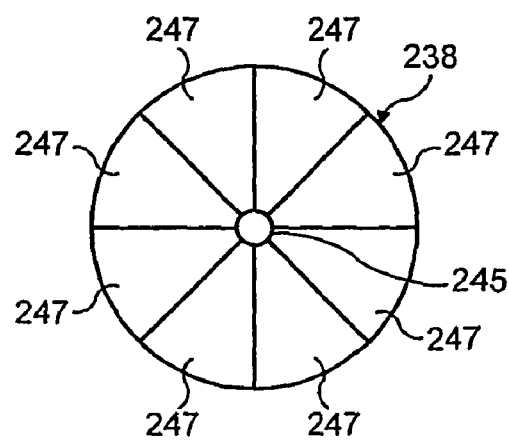
FIG. 11(c) illustrates one end view of the second rotatable element of the rotatable unit of the nasal delivery device of FIG. 11(a)
Figure 11D:
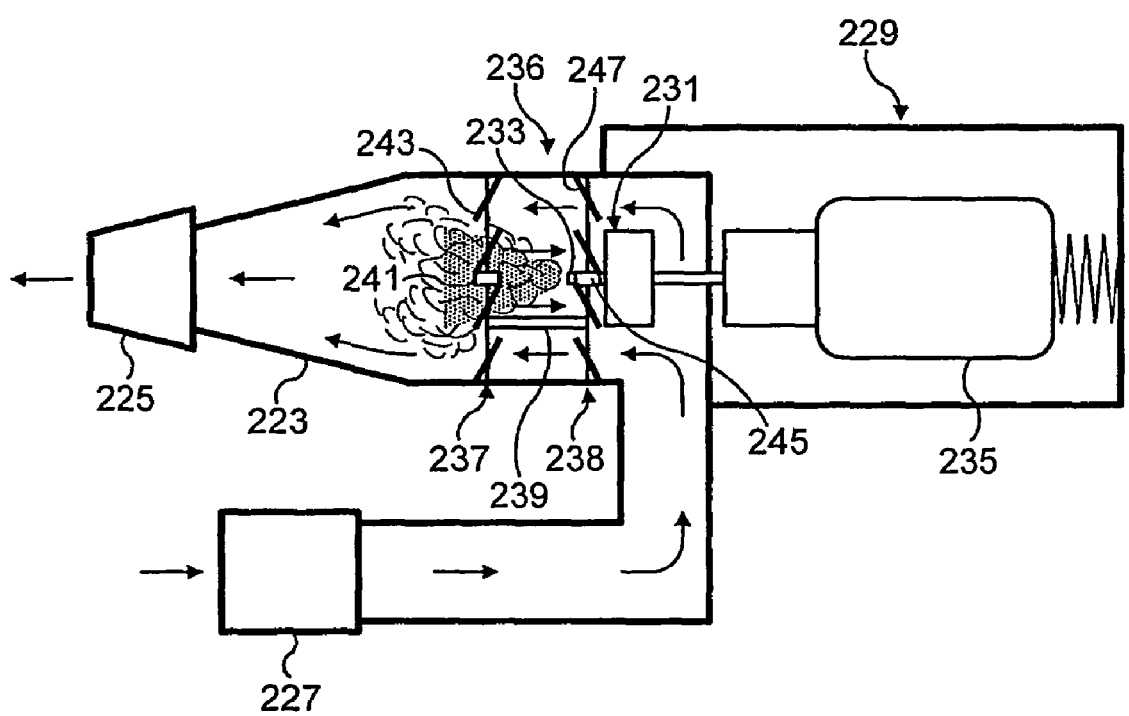
FIG. 11(d) illustrates the nasal delivery device of FIG. 11(a) in the actuated configuration.

FIGS. 10(a) to (c) illustrate a nasal delivery device in accordance with a ninth embodiment of the present invention.

The delivery device of this embodiment is very similar to the delivery device of the above-described eighth embodiment, and thus, in order to avoid unnecessary duplication of description, only the differences will be described in detail, with like reference signs designating like parts.

The delivery device of this embodiment differs from that of the above-described eighth embodiment in further comprising an exhalation breath actuatable gas delivery unit 214 for delivering a gas flow to the chamber 193 in response to exhalation by a subject, and in that the mouthpiece 197 is in fluid communication with the gas delivery unit 214 and not the chamber 193, whereby a gas flow is delivered to the chamber 193, and hence the nasal airway 1, in response to exhalation through the mouthpiece 197.

Operation of the delivery device is the same as for the above-described eighth embodiment, with a gas flow being delivered to the chamber 193, and hence the nasal airway 1, in response to exhalation through the mouthpiece 197.

FIGS. 11(a) to (d) illustrate a nasal delivery device in accordance with a tenth embodiment of the present invention.

The delivery device comprises a chamber 223, in this embodiment a substantially tubular member, into which an aerosol spray is delivered, a nosepiece 225 for fitting to a nostril of a subject which is in fluid communication with the chamber 223 and disposed to one, the downstream, end of the chamber 223, and a mouthpiece 227 through which the subject exhales and which is in fluid communication with the chamber 223.

The delivery device further comprises a delivery unit 229, in this embodiment a breath-actuated unit, for delivering an aerosol spray of substance into the chamber 223. The delivery unit 229 comprises a nozzle unit 231 which includes a nozzle 233 for delivering an aerosol spray of substance, and a substance supply unit 235 for delivering a metered dose of substance to the nozzle unit 231.

In this embodiment the nozzle 233 of the nozzle unit 231 is directed towards the nosepiece 225 and disposed so as to be co-axial therewith.

In this embodiment the substance supply unit 235 is an aerosol canister for delivering a metered volume of a propellant, preferably a hydrofluoroalkane (HFA) propellant or the like, containing substance, typically a medicament, either as a suspension or solution.

In an alternative embodiment the substance supply unit 235 could comprise a mechanical delivery pump, in particular a liquid delivery pump or a powder delivery pump, which delivers metered doses of substance on actuation thereof.

The delivery unit 229 is primeable, in this embodiment by loading a biasing element, and includes a release mechanism, which, when triggered, releases the biasing element and actuates the substance supply unit 235 to deliver a metered dose of substance.

The delivery device further comprises a rotatable unit 236 which comprises first and second rotatable elements 237, 238 which are coupled by a link 239 such as to rotate in unison.

One, the first, rotatable element 237 is disposed downstream of the nozzle 233 of the nozzle unit 231 such as to interact with an aerosol spray as generated from the nozzle 233, whereby an aerosol spray, when delivered from the nozzle 233, is acted upon by the first rotatable element 237, in this embodiment by reflection from the surface of the moving element 207 and interaction with an interacting air flow as generated thereby, such as to optimize characteristics of the aerosol spray, and in particular modify the particle size distribution of the particles of the aerosol spray and decelerate particles of the aerosol spray, which particles, once so optimized, are then entrained by the air flow through the chamber 223. The other, second rotatable element 238 is disposed upstream of the nozzle 233 of the nozzle unit 231 such as to be driven by a delivered gas flow, in this embodiment an exhaled air flow, which acts to drive the first rotatable element 237.

In this embodiment the first rotatable element 237 is mounted about a central pivot 241 and includes a plurality of vanes 243 which are inclined in one sense such that rotation of the first rotatable element 237 in one sense, in this embodiment in an anti-clockwise sense as viewed downstream, generates an interacting air flow in an upstream direction towards the nozzle 233 of the nozzle unit 231, which interacting air flow interacts with an aerosol spray as generated from the nozzle 233.

In this embodiment the second rotatable element 238 is mounted about a central pivot 245 and includes a plurality of vanes 247 which are inclined in the other, opposite sense to the vanes 243 of the first rotatable element 237 such that the exhaled air flow is such as to drive the second rotatable element 238 in the one sense, that is, in a counter-clockwise sense as viewed downstream. This rotation of the second rotatable element 238 directly effects rotation of the first rotatable element 237 in the same, one sense, which rotation of the first rotatable element 237 generates the interacting air flow in an upstream direction towards the nozzle 233 of the nozzle unit 231, which interacting air flow interacts with an aerosol spray as generated from the nozzle 233.

In this embodiment the first rotatable element 237 is configured to have a lesser resistance to air flow than the second rotatable element 238, and thereby the rotatable elements 237, 238 provide for a net flow through the chamber 223 and into the nasal airway 1 of the subject. In this embodiment the first rotatable element 237 includes vanes 243 having greater pitch than the vanes 247 of the second rotatable element 238. In an alternative embodiment the first rotatable element 237 could have a smaller diameter than the second rotatable element 238 such as to provide an annular flow path about the inner periphery of the chamber 223 for the exhaled air flow.

Operation of the delivery device will now be described hereinbelow.

Firstly, the nosepiece 225 is fitted to a nostril of a subject and the mouthpiece 227 is gripped in the lips of the subject.

The subject then begins to exhale through the mouthpiece 227, which exhalation acts to close the oropharyngeal velum of the subject and deliver an air flow through the chamber 223 and the nasal airway 1 of the subject, which air flow acts to rotate the rotatable unit 236 by the action of the air flow on the vanes 247 of the second rotatable element 238. This rotation of the rotatable unit 236 causes the first rotatable unit 237 to generate an interacting air flow in an upstream direction towards the nozzle 233 of the nozzle unit 231, which interacting air flow interacts with an aerosol spray as generated from the nozzle 233.

When a predetermined flow rate is achieved through the chamber 223, the substance supply unit 235 is actuated to deliver a metered dose of substance through the nozzle 233 of the nozzle unit 231, which nozzle 233 generates an aerosol spray in a direction towards the nosepiece 225. The aerosol spray, when delivered from the nozzle 233, is acted upon by the first rotatable element 237, through reflection therefrom and the interacting air flow generated thereby, such as to optimize characteristics of the particles thereof, in modifying the particle size distribution of the particles of the aerosol spray and decelerating the particles of the aerosol spray, which particles, as so optimized, are then entrained by the net air flow through the chamber 223.

In this way, the particles of the generated aerosol spray as delivered to the nasal airway 1 have optimized characteristics, and in particular an optimized particle size distribution and a much reduced velocity. Optimizing the particle size distribution of the aerosol spray provides for improved delivery to targeted sites in the nasal airway. In decelerating the particles of the aerosol spray, deposition on unwanted surfaces, which would result where the particles are delivered directly from the nozzle 233 of the nozzle unit 231 without intervention, is avoided.

Figure 12A:
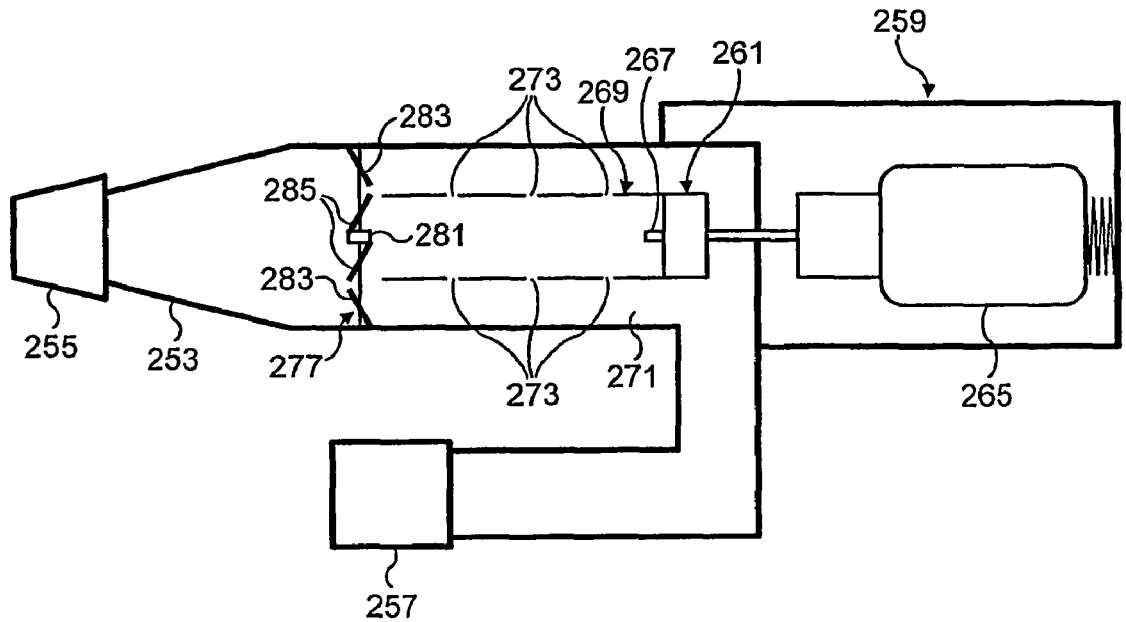
FIG. 12(a) illustrates a nasal delivery device in accordance with an eleventh embodiment of the present invention.
Figure 12B:
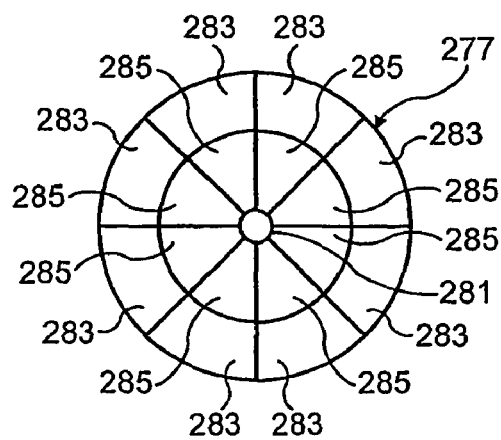
FIG. 12(b) illustrates one end view of the rotatable element of the nasal delivery device of FIG. 12(a)
Figure 12C:
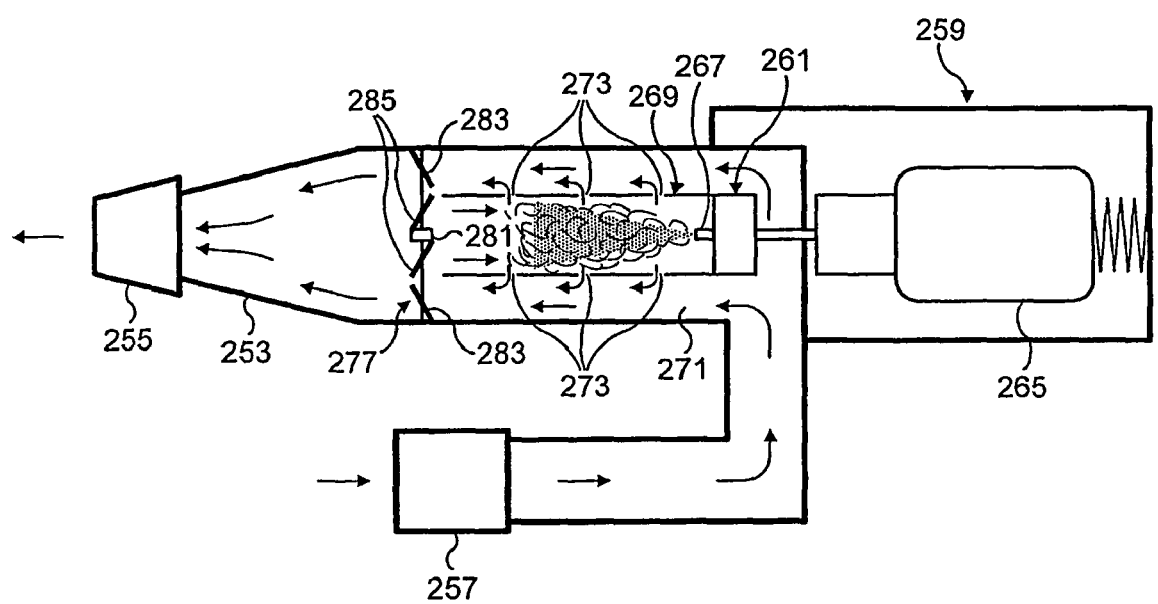
FIG. 12(c) illustrates the nasal delivery device of FIG. 12(a) in the actuated configuration.

FIGS. 12(a) to (c) illustrate a nasal delivery device in accordance with an eleventh embodiment of the present invention.

The delivery device comprises a chamber 253, in this embodiment a substantially tubular member, into which an aerosol spray is delivered, a nosepiece 255 for fitting to a nostril of a subject which is in fluid communication with the chamber 253 and disposed to one, the downstream, end of the chamber 253, and a mouthpiece 257 through which the subject exhales and which is in fluid communication with the chamber 253.

The delivery device further comprises a delivery unit 259 for delivering an aerosol spray of substance into the chamber 253. The delivery unit 259 comprises a nozzle unit 261 for delivering an aerosol spray of substance, and a substance supply unit 265 for delivering a metered dose of substance to the nozzle unit 261.

In this embodiment the nozzle unit 261 includes a nozzle 267 for delivering an aerosol spray of substance, and a tubular element 269 which extends forwardly of the nozzle 267 and is disposed concentrically within the chamber 253 such as to define an annular flow path 271 thereabout. The tubular element 269 includes a plurality of apertures 273 at spaced locations along the length thereof for providing a plurality of flow paths from within the tubular element 269 to the annular flow path 271.

In this embodiment the nozzle 267 of the nozzle unit 261 is directed towards the nosepiece 255 and disposed so as to be co-axial therewith.

In this embodiment the substance supply unit 265 is an aerosol canister for delivering a metered volume of a propellant, preferably a hydrofluoroalkane (HFA) propellant or the like, containing substance, typically a medicament, either as a suspension or solution.

In an alternative embodiment the substance supply unit 265 could comprise a mechanical delivery pump, in particular a liquid delivery pump or a powder delivery pump, which delivers metered doses of substance on actuation thereof.

The delivery unit 259 is primeable, in this embodiment by loading a biasing element, and includes a release mechanism, which, when triggered, releases the biasing element and actuates the substance supply unit 265 to deliver a metered dose of substance.

The delivery device further comprises a rotatable element 277 which is disposed at the distal end of the tubular element 269 of the nozzle unit 261.

In this embodiment the rotatable element 277 is mounted about a central pivot 281 and includes a plurality of first, outer vanes 283 which face the downstream end of the annular flow path 271 such as to be acted upon by the exhaled air flow, and a plurality of second, inner vanes 285 which are disposed radially inwardly of the outer vanes 283 and have a radial dimension corresponding to that of the tubular element 269 such as to face the downstream end of the tubular element 269. The outer vanes 283 of the rotatable element 277 are inclined in one sense such that the action of the exhaled air flow thereover causes the rotation of the rotatable element 277 in one sense, in this embodiment a counter-clockwise sense as viewed downstream. The inner vanes 285 of the rotatable element 277 are inclined in the other, opposite sense to the outer vanes 283 such that rotation of the rotatable element 277 in the one sense causes the inner vanes 285 to generate an interacting air flow in an upstream direction into the tubular element 269 and towards the nozzle 267 of the nozzle unit 261, which interacting air flow interacts with an aerosol spray as generated from the nozzle 267, thereby optimizing characteristics of the particles of the aerosol spray, in causing deceleration of the particles of the aerosol spray, and the decelerated aerosol at least in part being entrained by the interacting air streams through the apertures 273 in the tubular element 269 and into the annular flow channel 271 thereabout.

Operation of the delivery device will now be described hereinbelow.

Firstly, the nosepiece 255 is fitted to a nostril of a subject and the mouthpiece 257 is gripped in the lips of the subject.

The subject then begins to exhale through the mouthpiece 257, which exhalation acts to close the oropharyngeal velum of the subject and deliver an air flow through the chamber 253 via the annular flow channel 271 and the nasal airway 1 of the subject, which air flow acts to rotate the rotatable element 277 in the one sense, in this embodiment the counter-clockwise as viewed downstream, by the action of the exhaled air flow over the outer vanes 283 of the rotatable element 277. This rotation of the rotatable element 277 causes the inner vanes 285 to generate an interacting air flow in an upstream direction towards the nozzle 267 of the nozzle unit 261, which interacting air flow interacts with an aerosol spray as generated from the nozzle 267.

When a predetermined flow rate is achieved through the chamber 253, the substance supply unit 265 is actuated to deliver a metered dose of substance through the nozzle 267 of the nozzle unit 261, which nozzle 267 generates an aerosol spray in a direction towards the nosepiece 255. The aerosol spray, when delivered from the nozzle 267 of the nozzle unit 261, is acted on by the interacting air flow generated by the inner vanes 285 of the rotatable element 277 such as to decelerate the particles of the aerosol spray, and in a preferred embodiment modify the particle size distribution of the particles of the aerosol spray, which particles are then entrained by the interacting air flow as air flows through the apertures 273 in the tubular element 269 and into the annular flow channel 271 thereabout, and subsequently entrained by the exhaled air flow through the chamber 253 and the nasal airway 1 of the subject.

In this way, the particles of the generated aerosol spray as delivered to the nasal airway 1 have optimized characteristics, and in particular an optimized particle size distribution and a much reduced velocity. Optimizing the particle size distribution of the aerosol spray provides for improved delivery to targeted sites in the nasal airway. In decelerating the particles of the aerosol spray, deposition on unwanted surfaces, which would result where the particles are delivered directly from the nozzle 267 of the nozzle unit 261 without intervention, is avoided.

Finally, it will be understood that the present invention has been described in its preferred embodiments and can be modified in many different ways without departing from the scope of the invention as defined by the appended claims.

For example, the nasal delivery device of the above-described fourth embodiment could be modified in the manner of the above-described third embodiment, that is, to include an exhalation breath-actuatable gas supply unit 85 for delivering a gas flow through the chamber 93 which is separate to the exhalation breath of a subject.

In preferred embodiments the delivery devices are configured to deliver substance through one nostril of a subject at such a pressure as to flow around the posterior margin of the nasal septum 4 and out of the other nostril of the subject, thereby achieving bi-directional delivery through the nasal cavities 2, 3 as disclosed in WO-A-00/51672. In alternative embodiments the delivery devices can be configured to deliver substance at a reduced pressure which is not sufficient to achieve bi-directional delivery through the nasal cavities 2, 3.

The invention claimed is:

1. A nasal delivery device for delivering substance to a nasal airway of a subject, comprising:
    a mouthpiece through which a subject in use exhales;
    a nosepiece for fitting to a nostril of the subject;
    a delivery unit comprising a substance supply unit and a nozzle unit including at least one nozzle fluidly connected to the substance supply unit for generating an aerosol spray for delivery to a nasal airway of the subject; and
    an aerosol interactor operable to interact with an aerosol spray during generation from the at least one nozzle such as at least to modify the particle size distribution of particles of the aerosol spray, wherein the aerosol interactor is configured such that operation thereof is actuated prior to actuation of the delivery unit.

2. The delivery device of claim 1, wherein the at least one nozzle is configured such as to deliver the aerosol spray towards the nosepiece.

3. The delivery device of claim 1, wherein the aerosol interactor comprises a flow director for directing an interacting gas flow at the aerosol spray such as to interact with the same.

4. The delivery device of claim 3, wherein the flow director includes at least one flow-directing channel downstream of the at least one nozzle for directing an interacting gas flow and delivering at least one interacting gas stream to interact with the aerosol spray.

5. The delivery device of claim 4, wherein the at least one flow-directing channel has an annular outlet disposed about a delivery path of the aerosol spray.

6. The delivery device of claim 3, further comprising:
    a chamber in fluid communication with the nosepiece; and
    wherein the flow director includes an annular flow channel for providing an annular gas flow over an inner periphery of the chamber.

7. The delivery device of claim 6, wherein the chamber includes a flow deflector disposed at the inner periphery thereof and downstream of the at least one nozzle which is such as to obstruct the annular gas flow generated at the inner periphery of the chamber and cause the same to be deflected inwardly and generate a turbulent zone downstream of the at least one nozzle.

8. The delivery device of claim 7, wherein the flow deflector comprises an annular member.

9. The delivery device of claim 3, wherein the aerosol interactor comprises a flow director for directing an interacting gas flow at the aerosol spray such as to interact with the same, and further comprising:
   a gas supply unit for delivering a gas flow, the gas supply unit being fluidly connected to the flow director such that at least part of the delivered gas flow provides the interacting gas flow.

10. The delivery device of claim 1, wherein the aerosol interactor comprises a flow director for directing an interacting gas flow at the aerosol spray such as to interact with the same, and the mouthpiece is fluidly connected to the flow director such that at least part of the exhaled air flow provides the interacting gas flow.

11. The delivery device of claim 1, wherein the substance supply unit comprises an aerosol canister.

12. The delivery device of claim 1, wherein the substance supply unit comprises a delivery pump.

13. The delivery device of claim 12, wherein the delivery pump comprises a liquid spray pump.

14. A nasal delivery device for delivering substance to a nasal airway of a subject, comprising:
   a nosepiece for fitting to a nostril of a subject;
   a delivery unit comprising a substance supply unit and a nozzle unit including at least one nozzle fluidly connected to the substance supply unit for generating an aerosol spray for delivery to a nasal airway of the subject; and
   an aerosol interactor operable to interact with an aerosol spray during generation from the at least one nozzle such as at least to modify the particle size distribution of particles of the aerosol spray, wherein the aerosol interactor comprises a flow director which includes at least one flow-directing channel downstream of the at least one nozzle for directing an interacting gas flow and delivering at least one interacting gas stream to interact with the aerosol spray, and wherein the at least one flow-directing channel has an annular outlet disposed about a delivery path of the aerosol spray and the at least one flow-directing channel is configured such as to direct the at least one interacting gas stream substantially orthogonally to the delivery path of the aerosol spray.

15. A nasal delivery device for delivering substance to a nasal airway of a subject, comprising:
   a nosepiece for fitting to a nostril of a subject;
   a delivery unit comprising a substance supply unit and a nozzle unit including at least one nozzle fluidly connected to the substance supply unit for generating an aerosol spray for delivery to a nasal airway of the subject; and
   an aerosol interactor operable to interact with an aerosol spray during generation from the at least one nozzle such as at least to modify the particle size distribution of particles of the aerosol spray, wherein the aerosol interactor comprises a flow director which includes at least one flow-directing channel downstream of the at least one nozzle for directing an interacting gas flow and delivering at least one interacting gas stream to interact with the aerosol spray, and wherein the at least one flow-directing channel has an annular outlet disposed about a delivery path of the aerosol spray and the at least one flow-directing channel is configured such as to direct the at least one interacting gas stream in a direction inclined to the delivery path of the aerosol spray and away from the nosepiece.

16. The delivery device of claim 15, wherein the at least one flow-directing channel is an annular, frusto-conical channel configured to deliver a conical, annular interacting gas stream to the delivery path of the aerosol spray.

17. The delivery device of claim 16, wherein the at least one flow-directing channel is configured such that an apex of the conical, annular interacting gas stream delivered thereby is co-incident with the delivery path of the aerosol spray.

18. A nasal delivery device for delivering substance to a nasal airway of a subject, comprising:
   a nosepiece for fitting to a nostril of a subject;
   a delivery unit comprising a substance supply unit and a nozzle unit including at least one nozzle fluidly connected to the substance supply unit for generating an aerosol spray for delivery to a nasal airway of the subject; and
   an aerosol interactor operable to interact with an aerosol spray during generation from the at least one nozzle such as at least to modify the particle size distribution of particles of the aerosol spray, wherein the aerosol interactor comprises a flow director which includes a plurality of flow-directing channels in spaced relation downstream of the at least one nozzle for directing an interacting gas flow and delivering a plurality of interacting gas streams to interact with the aerosol spray.

19. A nasal delivery device for delivering substance to a nasal airway of a subject, comprising:
   a mouthpiece through which a subject in use exhales;
   a chamber into which an aerosol spray is delivered;
   a nosepiece for fitting to a nostril of the subject and being in fluid communication with the chamber;
   a delivery unit comprising a substance supply unit and a nozzle unit including at least one nozzle fluidly connected to the substance supply unit for generating an aerosol spray into the chamber for delivery to a nasal airway of the subject; and
   an aerosol interactor operable to interact with an aerosol spray as generated by the at least one nozzle, wherein the aerosol interactor comprises a movable element disposed downstream of the at least one nozzle and being moved by a gas flow delivered through the chamber.

20. The delivery device of claim 19, wherein the aerosol interactor is disposed in opposed relation to the at least one nozzle.

21. The delivery device of claim 20, wherein the aerosol interactor is configured such as to present a continuous surface to the aerosol spray.

22. The delivery device of claim 19, wherein the aerosol interactor is disposed relative to the at least one nozzle such that the aerosol spray is reflected thereby.

23. The delivery device of claim 19, wherein the movable element comprises a rotatable element.

24. A nasal delivery device for delivering substance to a nasal airway of a subject, comprising:
   a nosepiece for fitting to a nostril of a subject;
   a delivery unit comprising a substance supply unit and a nozzle unit including at least one nozzle fluidly connected to the substance supply unit for generating an aerosol spray for delivery to a nasal airway of the subject; and
   an aerosol interactor operable to interact with an aerosol spray as generated by the at least one nozzle, wherein the aerosol interactor comprises a movable element disposed downstream of the at least one nozzle, and the movable element comprises first and second rotatable elements coupled so as to rotate in unison, the first rotatable element including vanes oriented in one sense such as to be rotated in one sense by a gas flow thereover, and the second rotatable element being disposed downstream of the at least one nozzle and including vanes oriented in the other, opposite sense to the vanes of the first rotatable element such as to generate an interacting gas flow in an upstream direction towards the at least one nozzle on being rotated in the one sense by rotation of the first rotatable element.

25. The delivery device of claim 24, wherein the first rotatable element is disposed upstream of the at least one nozzle.

26. A nasal delivery device for delivering substance to a nasal airway of a subject, comprising:
 a nosepiece for fitting to a nostril of a subject;
 a delivery unit comprising a substance supply unit and a nozzle unit including at least one nozzle fluidly connected to the substance supply unit for generating an aerosol spray for delivery to a nasal airway of the subject, wherein the nozzle unit includes a tubular element which extends downstream of the at least one nozzle and includes a plurality of apertures for providing a plurality of flow paths therethrough; and
 an aerosol interactor operable to interact with an aerosol spray as generated by the at least one nozzle, wherein the aerosol interactor comprises a movable element disposed downstream of the at least one nozzle, and the aerosol interactor comprises a rotatable element disposed at a downstream end of the tubular element, the rotatable element including first, outer vanes oriented in one sense and disposed radially beyond the tubular element such that the rotatable element is rotated in one sense by a gas flow thereover, and second, inner vanes oriented in the other, opposite sense to the outer vanes such as to generate an interacting gas flow in an upstream direction towards the at least one nozzle with rotation of the rotatable element, which interacting gas flow is such as to interact with the aerosol spray and pass through the apertures in the tubular element.

27. A method of delivering substance to a nasal airway of a subject, comprising the steps of:
 a subject exhaling through a mouthpiece;
 fitting a nosepiece to a nostril of the subject;
 actuating a delivery unit to generate an aerosol spray from at least one nozzle for delivery to a nasal airway of the subject; and
 operating an aerosol interactor to interact with an aerosol spray as generated by the at least one nozzle, wherein operation of the aerosol interactor is actuated prior to actuation of the delivery unit.

28. The method of claim 27, wherein the aerosol spray is delivered towards the nosepiece.

29. The method of claim 27, wherein the aerosol interactor comprises a flow director; and
 the step of operating the aerosol interactor comprises the step of:
 directing an interacting gas flow at the aerosol spray such as to interact with the same.

30. The method of claim 29, wherein the flow director includes at least one flow-directing channel downstream of the at least one nozzle, and
 the step of operating the aerosol interactor comprises the step of:
 directing an interacting gas flow to deliver at least one interacting gas stream to interact with the aerosol spray.

31. The method of claim 30, wherein the at least one flow-directing channel has an annular outlet disposed about a delivery path of the aerosol spray.

32. The method of claim 29, wherein the aerosol spray is delivered into a chamber in fluid communication with the nosepiece; and
 further comprising the step of:
 providing an annular gas flow over an inner periphery of the chamber.

33. The method of claim 32, wherein the chamber includes a flow deflector disposed at the inner periphery thereof and downstream of the at least one nozzle; and
 further comprising the step of:
 obstructing the annular gas flow generated at the inner periphery of the chamber such as to cause the same to be deflected inwardly and generate a turbulent zone downstream of the at least one nozzle.

34. The method of claim 33, wherein the flow deflector comprises an annular member.

35. The method of claim 29, wherein the aerosol interactor comprises a flow director, and the step of operating the aerosol interactor comprises the step of:
 directing an interacting gas flow to deliver at least one interacting gas stream to interact with the same, and
 further comprising the step of:
 supplying a gas flow from a gas supply unit, at least part of the supplied gas flow being delivered to the flow director as the interacting gas flow.

36. The method of claim 27, wherein the aerosol interactor comprises a flow director, and the step of operating the aerosol interactor comprises the step of:
 directing an interacting gas flow to deliver at least one interacting gas stream to interact with the same, wherein the mouthpiece is fluidly connected to the flow director such that at least part of the exhaled air flow provides the interacting gas flow.

37. The method of claim 27, wherein the aerosol spray is from an aerosol canister.

38. The method of claim 27, wherein the aerosol spray is from a delivery pump.

39. The method of claim 38, wherein the delivery pump comprises a liquid spray pump.

40. A method of delivering substance to a nasal airway of a subject, comprising the steps of:
 fitting a nosepiece to a nostril of a subject;
 actuating a delivery unit to generate an aerosol spray from at least one nozzle for delivery to a nasal airway of the subject; and
 operating an aerosol interactor to interact with an aerosol spray as generated by the at least one nozzle, wherein the aerosol interactor comprises a flow director which includes at least one flow-directing channel downstream of the at least one nozzle, the at least one flow-directing channel having an annular outlet disposed about a delivery path of the aerosol spray, and wherein operation of the aerosol interactor comprises directing an interacting gas flow to deliver at least one interacting gas stream substantially orthogonally to the delivery path of the aerosol spray to interact with the aerosol spray.

41. A method of delivering substance to a nasal airway of a subject, comprising the steps of:
 fitting a nosepiece to a nostril of a subject;
 actuating a delivery unit to generate an aerosol spray from at least one nozzle for delivery to a nasal airway of the subject; and
 operating an aerosol interactor to interact with an aerosol spray as generated by the at least one nozzle, wherein the aerosol interactor comprises a flow director which includes at least one flow-directing channel downstream of the at least one nozzle, the at least one flow-directing channel having an annular outlet disposed about a delivery path of the aerosol spray, and wherein operation of the aerosol interactor comprises directing an interacting gas flow to deliver at least one interacting gas stream in a direction inclined to the delivery path of the aerosol spray and away from the nosepiece to interact with the aerosol spray.

42. The method of claim 41, wherein the at least one interacting gas stream is a conical, annular interacting gas stream.

43. The method of claim 42, wherein an apex of the conical, annular interacting gas stream is co-incident with the delivery path of the aerosol spray.

44. A method of delivering substance to a nasal airway of a subject, comprising the steps of:
fitting a nosepiece to a nostril of a subject;
actuating a delivery unit to generate an aerosol spray from at least one nozzle for delivery to a nasal airway of the subject; and
operating an aerosol interactor to interact with an aerosol spray as generated by the at least one nozzle, wherein the aerosol interactor comprises a flow director which includes a plurality of flow-directing channels in spaced relation downstream of the at least one nozzle, wherein operation of the aerosol interactor comprises directing an interacting gas flow to deliver a plurality of interacting gas streams to interact with the aerosol spray.

45. A method of delivering substance to a nasal airway of a subject, comprising the steps of:
a subject exhaling through a mouthpiece;
fitting a nosepiece to a nostril of the subject;
actuating a delivery unit to generate an aerosol spray from at least one nozzle into a chamber in fluid communication with the nosepiece for delivery to a nasal airway of the subject; and
operating an aerosol interactor to interact with an aerosol spray as generated by the at least one nozzle, wherein the aerosol interactor comprises a movable element disposed downstream of the at least one nozzle; and
the step of operating the aerosol interactor comprises the step of:
delivering a gas flow through the chamber to move the movable element downstream of the at least one nozzle such as to interact with the aerosol spray.

46. The method of claim 45, wherein the aerosol interactor is disposed in opposed relation to the at least one nozzle.

47. The method of claim 46, wherein the aerosol interactor is configured such as to present a continuous surface to the aerosol spray.

48. The method of claim 46, wherein the aerosol interactor is disposed relative to the at least one nozzle such that the aerosol spray is reflected thereby.

49. The method of claim 45, wherein the movable element comprises a rotatable element.

50. A method of delivering substance to a nasal airway of a subject, comprising the steps of:
fitting a nosepiece to a nostril of a subject;
actuating a delivery unit to generate an aerosol spray from at least one nozzle for delivery to a nasal airway of the subject; and operating an aerosol interactor to interact with an aerosol spray as generated by the at least one nozzle, wherein the aerosol interactor comprises a movable element disposed downstream of the at least one nozzle, and the movable element comprises first and second rotatable elements coupled so as to rotate in unison, the first rotatable element including vanes oriented in one sense such as to be rotated in one sense by a gas flow thereover, and the second rotatable element being disposed downstream of the at least one nozzle and including vanes oriented in the other, opposite sense to the vanes of the first rotatable element such as to generate an interacting gas flow in an upstream direction towards the at least one nozzle on being rotated in the one sense by rotation of the first rotatable element, and the step of operating the aerosol interactor comprises the step of:
driving a gas flow over the first rotatable element such as to cause rotation of the same and thereby rotate the second rotatable element such as to generate an interacting gas flow in an upstream direction towards the at least one nozzle which interacts with the aerosol spray.

51. The method of claim 50, wherein the first rotatable element is disposed upstream of the at least one nozzle.

52. A method of delivering substance to a nasal airway of a subject, comprising the steps of:
fitting a nosepiece to a nostril of a subject;
actuating a delivery unit to generate an aerosol spray from at least one nozzle for delivery to a nasal airway of the subject, wherein the step of actuating the delivery unit to generate an aerosol spray comprises the step of:
actuating the delivery unit to generate an aerosol spray from at least one nozzle into a tubular element which extends downstream of the at least one nozzle, the tubular element including a plurality of apertures for providing a plurality of flow paths therethrough; and
operating an aerosol interactor to interact with an aerosol spray as generated by the at least one nozzle, wherein the aerosol interactor comprises a movable element disposed downstream of the at least one nozzle, and the step of operating the aerosol interactor comprises the steps of:
moving a rotatable element disposed at a downstream end of the tubular element, the rotatable element including first, outer vanes oriented in one sense and disposed radially beyond the tubular element such that the rotatable element is rotated in one sense by a gas flow thereover, and second, inner vanes oriented in the other, opposite sense to the outer vanes such as to generate an interacting gas flow in an upstream direction towards the at least one nozzle with rotation of the rotatable element; and
driving a gas flow over the outer vanes of the rotatable element to cause rotation of the same and thereby cause the inner vanes of the rotatable element to generate an interacting gas flow in an upstream direction towards the at least one nozzle, which interacting gas flow is such as to interact with the aerosol spray and pass through the apertures in the tubular element.

* * * * *